(12) United States Patent
Astrid et al.

(10) Patent No.: US 9,719,054 B2
(45) Date of Patent: *Aug. 1, 2017

(54) METALLOPROTEASES FROM ALICYCLOBACILLUS

(71) Applicant: Novozymes A/S, Bagsvaerd (DK)

(72) Inventors: Benie Astrid, Vaerloese (DK); Peter Rahbek Oestergaard, Virum (DK); Morten Gjermansen, Greve (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/063,964

(22) Filed: Mar. 8, 2016

(65) Prior Publication Data

US 2016/0177239 A1      Jun. 23, 2016

Related U.S. Application Data

(62) Division of application No. 14/421,078, filed as application No. PCT/EP2013/067412 on Aug. 21, 2013, now Pat. No. 9,315,791.

(60) Provisional application No. 61/692,057, filed on Aug. 22, 2012.

(30) Foreign Application Priority Data

Aug. 22, 2012   (EP) .................................... 12181360

(51) Int. Cl.
```
C11D 3/386   (2006.01)
C12N 15/63   (2006.01)
C12N 1/14    (2006.01)
C12N 1/20    (2006.01)
D06M 16/00   (2006.01)
C12N 9/54    (2006.01)
C12N 9/50    (2006.01)
```

(52) U.S. Cl.
CPC .......... C11D 3/386 (2013.01); C11D 3/38618 (2013.01); C12N 1/14 (2013.01); C12N 1/20 (2013.01); C12N 9/50 (2013.01); C12N 9/54 (2013.01); C12N 15/63 (2013.01); D06M 16/003 (2013.01); C12Y 304/24 (2013.01)

(58) Field of Classification Search
None
See application file for complete search history.

(56) References Cited

U.S. PATENT DOCUMENTS 9,315,791 B2 *   4/2016  Benie ................... C12N 9/50
2008/0293610 A1  11/2008 Shaw

FOREIGN PATENT DOCUMENTS

| EP | 0316725 A2    | 5/1989  |
|----|---------------|---------|
| EP | 1288282 A1    | 3/2003  |
| WO | 00/37486 A1   | 6/2000  |
| WO | 00/60042 A1   | 10/2000 |
| WO | 2007/044993 A2| 4/2007  |
| WO | 2009/058518 A1| 5/2009  |

OTHER PUBLICATIONS

Alexandrov et al., GenBank Accession No. BAJ01810 (2010).
Hoogaars et al., Genbank Accession No. BAD13318.1 (2012).
Ma et al, UniProt Accession No. H6NEM9 (2014).
Shaw et al., Geneseq Access No. ANJ68750 (2007).
Zwick et al., Genbank Accession No. EEK52561.1 (2009).
Ma et al, 2012, GenBank access No. AFC28333.1.

\* cited by examiner

Primary Examiner — Robert Mondesi
Assistant Examiner — Richard Ekstrom
(74) Attorney, Agent, or Firm — David Fazzolare

(57) ABSTRACT

The present invention relates to new metalloproteases derived from *Alicyclobacillus* and the use thereof in cleaning processes, such as laundry and dish wash, and in particular to the use in low temperature wash and in removal of egg stains. The invention also relates to detergent compositions and cleaning compositions comprising *Alicyclobacillus* sp. metalloproteases.

11 Claims, No Drawings

METALLOPROTEASES FROM ALICYCLOBACILLUS

CROSS-REFERENCE TO RELATED APPLICATIONS

This application is a divisional of U.S. application Ser. No. 14/421,078 filed on Feb. 11, 2015, now pending, which is a 35 U.S.C. 371 national application of PCT/EP2013/067412 filed Aug. 21, 2013, which claims priority or the benefit under 35 U.S.C. 119 of European application no. 12181360.4 filed Aug. 22, 2012 and U.S. provisional application No. 61/692,057 filed Aug. 22, 2012. The contents of these applications are fully incorporated herein by reference.

REFERENCE TO SEQUENCE LISTING

This application contains a Sequence Listing in computer readable form, which is incorporated herein by reference.

FIELD OF THE INVENTION

The present invention relates to cleaning and/or detergent compositions comprising metalloproteases (E.C 3.4.24). The invention further concerns new metalloproteases from *Alicyclobacillus* sp. and the use of thereof in cleaning processes, such as dish wash and laundry. Further the invention concerns methods of doing cleaning, such as dish wash and laundry.

BACKGROUND OF THE INVENTION

The detergent industry has for more than 30 years implemented different enzymes in detergent formulations, most commonly used enzymes includes proteases, amylases and lipases each adapted for removing various types of stains. In addition to the enzymes detergent compositions typically include a complex combination of ingredients. For example, most cleaning products include surfactant system, bleaching agents or builders. Despite the complexity of current detergents, there remains a need for developing new detergent compositions comprising new enzymes and/or enzyme blends.

Metalloproteases are proteolytic enzymes having an absolute requirement for metal ion for their activity. Most metalloproteases are zinc-dependent, although some use other transition metals. Metalloproteases have been widely used in different industries like food and brewing industry. One group of metalloproteases is the M4 family metalloproteases which have been used, in various applications. For example, the M4 metalloprotease known as Thermolysin has been used as a nonspecific proteinase to obtain fragments for peptide sequencing such as described in, e.g., EP 0 316 725. It has also been used as a peptide synthetase as described in WO 00/37486, disclosing a method for production of the artificial sweetener aspartame. Another M4 metalloprotease is the *Bacillus amyloliquefaciens* metalloprotease, also known as Neutrase®, which has been used for many years as an additive in various food and feed products and, e.g., in brewing. This metalloprotease has also been described for use in detergent and cleaning compositions and processes as described, e.g., in WO 2007/044993, use of storage-stable metalloproteases in detergent or WO 2009/058518, and EP 1 288 282 (Unilever), which describes a blend of a metalloprotease and a serine protease for use in dish washing. WO 00/60042 also describes detergent compositions containing a metalloprotease.

However, the use of metalloproteases in the detergent industry has been very limited and focus has been on the use of the metalloproteases Neutrase® and/or "NprE" as set forth in WO 2007/044993. Generally, metalloproteases are very unstable under conventional wash conditions and in conventional detergent compositions. Thus, the use of metalloproteases in wash and cleaning processes and in detergents has been limited.

The increased focus on improving the washing processes in order to make them more environmental friendly has resulted in a global tendency to lowering wash time, pH and temperature, decreasing the amount of detergent components which may influence the environment negatively. The present invention is directed to these and other important ends.

SUMMARY OF THE INVENTION

The present invention relates to an isolated polypeptide having protease activity selected from the group consisting of:

a. a polypeptide having at least 60% sequence identity, at least 65% sequence identity, at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity or at least 99% sequence identity to the mature polypeptide of SEQ ID NO: 2 or SEQ ID NO: 4;

b. a polypeptide encoded by a polynucleotide that hybridizes under medium stringency conditions with (i) the mature polypeptide coding sequence of SEQ ID NO: 1 or SEQ ID NO: 3, (ii) the cDNA sequence comprising the mature polypeptide coding sequence of SEQ ID NO: 1 or SEQ ID NO: 3, or (iii) the full-length complementary strand of (i) or (ii);

c. a polypeptide encoded by a polynucleotide having at least 60% sequence identity, at least 65% sequence identity, at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity or at least 99% sequence identity to the mature polypeptide coding sequence of SEQ ID NO: 1 or SEQ ID NO: 3:

d. a variant comprising a substitution, deletion, and/or insertion of one or more (e.g. several) amino acids of the mature polypeptide of SEQ ID NO: 2 or SEQ ID NO: 4; and e. a fragment of a polypeptide of (a), (b), (c), or (d) that has protease activity.

The isolated polypeptide of the invention is a metalloprotease belonging to the M4 metalloprotease group. Preferably the isolated polypeptide is derived from *Alicyclobacillus* sp.

The invention further relates to compositions comprising the isolated polypeptide of the invention, in particular detergent compositions, and the use of such composition in a cleaning process such as laundry and hard surface cleaning e.g. automated dish wash.

In a particular embodiment, the invention relates to polynucleotides encoding the polypeptides of the invention, constructs, expression vectors and host cells comprising such polynucleotides and the use thereof for the production of the polypeptide of the invention.

In a further embodiment the invention also relates to new signal peptide and propeptides derived from *Alicyclobacil-*

*lus* sp. and the use thereof for producing the polypeptide of the invention or another polypeptide.

DETAILED DESCRIPTION OF THE INVENTION

Definitions

The term "protease activity" or "peptidase activity" is defined herein as the ability to break down the amide bond of a protein by hydrolysis of the peptide bonds that link amino acids together in a polypeptide chain.

The term "metalloprotease" as used herein refers to a protease having one or more metal ions in the binding/active site.

The term "M4 Metalloprotease Family" or "M4 Metalloprotease" or "M4" as used herein means a polypeptide falling into the M4 metalloprotease family according to Rawlings et al., *Biochem. J.* 290, 205-218 (1993) and as further described in MEROPS (Rawlings et al., MEROPS: the peptidase database, *Nucl. Acids Res.* 34 Database issue, D270-272, 2006). The M4 metalloproteases are neutral metalloproteases containing mainly endopeptidases. All peptidases in the family bind a single, catalytic zinc ion. M4 metalloprotease family members include the common HEXXH motif, where the histidine residues serve as zinc ligands and glutamate is an active site residue. M4 metalloproteases have a pH optimum mainly at neutral pH. The M4 metalloprotease family includes, e.g., Neutrase® (classified as MEROPS subclass M04.014), Thermolysin, Bacillolysin, vibriolysin, pseudolysin, Msp peptidase, coccolysin, aureolysin, vimelysin, lambda toxin neutral peptidase B, PA peptidase (*Aeromonas*-type), griselysin, stearolysin, MprIII (*Alteromonas* sp. strain O-7), pap6 peptidase, neutral peptidase (*Thermoactinomyces*-type), ZmpA peptidase (*Burkholderia* sp.), zpx peptidase, PrtS peptidase (*Photorhabdus luminescens*), protealysin, ZmpB peptidase (*Burkholderia* sp.). The M4 metalloprotease family of polypeptides have been further characterized and presently includes, according to MEROPS, at least twenty-two subclasses for which a distinct MEROPS ID (i.e., an identifier of the formula M04.xxx) has been assigned, as well as non-peptidase homologues and unassigned peptidases.

The term "isolated polypeptide" as used herein refers to a polypeptide that is isolated from a source. In one aspect, the variant or polypeptide is at least 20% pure, more preferably at least 40% pure, more preferably at least 60% pure, even more preferably at least 80% pure, most preferably at least 90% pure and even most preferably at least 95% pure, as determined by SDS-PAGE.

The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form. This can be accomplished, for example, by preparing the polypeptide by well-known recombinant methods or by classical purification methods.

The term "mature polypeptide coding sequence" means a polynucleotide that encodes a mature polypeptide having protease activity.

The relatedness between two amino acid sequences or between two nucleotide sequences is described by the parameter "sequence identity". For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277; emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra; emboss.org), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

The term "fragment" means a polypeptide having one or more (several) amino acids deleted from the amino and/or carboxyl terminus of a mature polypeptide; wherein the fragment has protease activity.

The term "functional fragment of a polypeptide" or "functional fragment thereof" is used to describe a polypeptide which is derived from a longer polypeptide, e.g., a mature polypeptide, and which has been truncated either in the N-terminal region or the C-terminal region or in both regions to generate a fragment of the parent polypeptide. To be a functional polypeptide the fragment must maintain at least 20%, preferably at least 40%, more preferably at least 50%, more preferably at least 60%, more preferably at least 70%, more preferably at least 80%, even more preferably at least 90%, most preferably at least 95%, and even most preferably at least 100% of the protease activity of the full-length/mature polypeptide. An M4 metalloprotease may be truncated such that certain domain is removed to generate a functional fragment, which may be polypeptides where less than 200 amino acids have been removed from the mature M4 Metalloprotease, preferably less than 150 amino acids, more preferably less than 120, 100, 80, 60, 40, 30 amino acids, even more preferably less than 20 amino acids and most preferably less than 10 amino acids have been removed from the mature polypeptide.

The term "subsequence" means a polynucleotide having one or more (several) nucleotides deleted from the 5' and/or 3' end of a mature polypeptide coding sequence; wherein the subsequence encodes a fragment having protease activity.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "variant" means a polypeptide having metalloprotease activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

The terms "cleaning compositions" and "cleaning formulations," refer to compositions that find use in the removal of undesired compounds from items to be cleaned, such as fabric, carpets, dishware including glassware, contact lenses, hard surfaces such as tiles, zincs, floors, and table surfaces, hair (shampoos), skin (soaps and creams), teeth (mouthwashes, toothpastes), etc. The terms encompasses any materials/compounds selected for the particular type of cleaning composition desired and the form of the product (e.g., liquid, gel, granule, or spray compositions), as long as the composition is compatible with the metalloprotease and other enzyme(s) used in the composition. The specific selection of cleaning composition materials is readily made by considering the surface, item or fabric to be cleaned, and the desired form of the composition for the cleaning conditions during use. These terms further refer to any composition that is suited for cleaning, bleaching, disinfecting, and/or sterilizing any object and/or surface. It is intended that the terms include, but are not limited to detergent composition (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

The term "detergent composition", includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types.

The terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. It is intended that in addition to the metalloprotease according to the invention, the term encompasses detergents that contains, e.g., surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, and corrosion agents, enzyme inhibitors or stabilizers, enzyme activators, transferase(s), hydrolytic enzymes, oxido reductases, bluing agents and fluorescent dyes, antioxidants, and solubilizers.

The term "fabric" encompasses any textile material. Thus, it is intended that the term encompass garments, as well as fabrics, yarns, fibers, non-woven materials, natural materials, synthetic materials, and any other textile material.

The term "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers. The term, "textile materials" is a general term for fibers, yarn intermediates, yarn, fabrics, and products made from fabrics (e.g., garments and other articles).

The term "non-fabric detergent compositions" include non-textile surface detergent compositions, including but not limited to dishwashing detergent compositions, oral detergent compositions, denture detergent compositions, and personal cleansing compositions.

The term "effective amount of enzyme" refers to the quantity of enzyme necessary to achieve the enzymatic activity required in the specific application, e.g., in a defined detergent composition. Such effective amounts are readily ascertained by one of ordinary skill in the art and are based on many factors, such as the particular enzyme used, the cleaning application, the specific composition of the detergent composition, and whether a liquid or dry (e.g., granular, bar) composition is required, and the like. The term "effective amount" of a metalloprotease refers to the quantity of metalloprotease described hereinbefore that achieves a desired level of enzymatic activity, e.g., in a defined detergent composition.

The term "wash performance" of an enzyme refers to the contribution of an enzyme to washing that provides additional cleaning performance to the detergent without the addition of the enzyme to the composition. Wash performance is compared under relevant washing conditions. Wash performance of enzymes is conveniently measured by their ability to remove certain representative stains under appropriate test conditions. In these test systems, other relevant factors, such as detergent composition, detergent concentration, water hardness, washing mechanics, time, pH, and/or temperature, can be controlled in such a way that conditions typical for household application in a certain market segment are imitated.

The term "water hardness" or "degree of hardness" or "dH" or "°dH" as used herein refers to German degrees of hardness. One degree is defined as 10 milligrams of calcium oxide per liter of water.

The term "relevant washing conditions" is used herein to indicate the conditions, particularly washing temperature, time, washing mechanics, detergent concentration, type of detergent and water hardness, actually used in households in a detergent market segment.

The term "improved property" is used to indicate that a better end result is obtained in a property compared to the same process performed without the enzyme. Exemplary properties which are preferably improved in the processes of the present invention include wash performance, enzyme stability, enzyme activity and substrate specificity.

The term "improved wash performance" is used to indicate that a better end result is obtained in stain removal from items washed (e.g., fabrics or dishware and/or cutlery) under relevant washing conditions as compared to no enzyme or to a reference enzyme, or that less enzyme, on weight basis, is needed to obtain the same end result relative to no enzyme or to a reference enzyme. Improved wash performance could in this context also be that the same effect, e.g., stain removal effect is obtained in shorter wash time, e.g., the enzymes provide their effect more quickly under the tested conditions.

The term "retained wash performance" is used to indicate that the wash performance of an enzyme, on weight basis, is at least 80 percent relative to another enzyme under relevant washing conditions.

The term "enzyme detergency" or "detergency" or "detergency effect" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process an effect that also is termed anti-redeposition, restoring fully or partly the whiteness of textiles, which originally were white but after repeated use and wash have obtained a greyish or yellowish appearance an effect that also is termed whitening. Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric an effect that is also termed dye transfer inhibition or anti-back staining, removal of protruding or broken fibers from a fabric surface to decrease pilling tendencies or remove already existing pills or fuzz an effect that also is termed anti-pilling, improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching component such as hydrogen peroxide or other peroxides.

The term "anti-redeposition" as used herein describes the reduction or prevention of redeposition of soils dissolved or suspended in the wash liquor onto the cleaned objects. Redeposition may be seen after one or multiple washing cycles (e.g., as a greying, yellowing or other discolorations).

The term "adjunct materials" means any liquid, solid or gaseous material selected for the particular type of detergent composition desired and the form of the product (e.g., liquid, granule, powder, bar, paste, spray, tablet, gel, or foam composition), which materials are also preferably compatible with the metalloprotease enzyme used in the composition. In some embodiments, granular compositions are in "compact" form, while in other embodiments, the liquid compositions are in a "concentrated" form.

The term "stain removing enzyme" as used herein, describes an enzyme that aids the removal of a stain or soil from a fabric or a hard surface. Stain removing enzymes act on specific substrates, e.g., protease on protein, amylase on starch, lipase and cutinase on lipids (fats and oils), pectinase on pectin and hemicellulases on hemicellulose. Stains are often depositions of complex mixtures of different components which either results in a local discolouration of the material by itself or which leaves a sticky surface on the object which may attract soils dissolved in the washing liquor thereby resulting in discolouration of the stained area. When an enzyme acts on its specific substrate present in a stain the enzyme degrades or partially degrades its substrate thereby aiding the removal of soils and stain components associated with the substrate during the washing process. For example, when a protease acts on a grass stain it degrades the protein components in the grass and allows the green/brown colour to be released during washing.

The term "reduced amount" means in this context that the amount of the component is smaller than the amount which would be used in a reference process under otherwise the same conditions. In a preferred embodiment the amount is reduced by, e.g., at least 5%, such as at least 10%, at least 15%, at least 20% or as otherwise herein described.

The term "low detergent concentration" system includes detergents where less than about 800 ppm of detergent components are present in the wash water. Asian, e.g., Japanese detergents are typically considered low detergent concentration systems.

The term "medium detergent concentration" system includes detergents wherein between about 800 ppm and about 2000 ppm of detergent components are present in the wash water. North American detergents are generally considered to be medium detergent concentration systems.

The term "high detergent concentration" system includes detergents wherein greater than about 2000 ppm of detergent components are present in the wash water. European detergents are generally considered to be high detergent concentration systems.

Polypeptides Having Protease Activity

The present invention relates to isolated polypeptides having protease activity selected from the group consisting of:

(a) a polypeptide having at least 60% sequence identity, at least 65% sequence identity, at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity or at least 99% sequence identity to the mature polypeptide of SEQ ID NO: 2 or SEQ ID NO: 4;

(b) a polypeptide encoded by a polynucleotide that hybridizes under medium stringency conditions with (i) the mature polypeptide coding sequence of SEQ ID NO: 1 or SEQ ID NO: 3, (ii) the cDNA sequence comprising the mature polypeptide coding sequence of SEQ ID NO: 1 or SEQ ID NO: 3, or (iii) the full-length complementary strand of (i) or (ii);

(c) a polypeptide encoded by a polynucleotide having at least 60% sequence identity, at least 65% sequence identity, at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity or at least 99% sequence identity to the mature polypeptide coding sequence of SEQ ID NO: 1 or SEQ ID NO: 3;

(d) a variant comprising a substitution, deletion, and/or insertion of one or more (e.g. several) amino acids of the mature polypeptide of SEQ ID NO: 2 or SEQ ID NO: 4; and (e) a fragment of a polypeptide of (a), (b), (c), or (d) that has protease activity.

The present invention relates to isolated polypeptides or catalytic domains having a sequence identity to the mature polypeptide of SEQ ID NO: 2 or SEQ ID NO: 4 of at least 60%, e.g., at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than ten amino acids, e.g., by five amino acids, by four amino acids, by three amino acids, by two amino acids, and by one amino acid from the mature polypeptide of SEQ ID NO: 2 or SEQ ID NO: 4.

A polypeptide of the present invention preferably comprises or consists of the amino acid sequence of SEQ ID NO: 2 or SEQ ID NO: 4 or an allelic variant thereof; or is a fragment thereof having protease activity. In another aspect, the polypeptide comprises or consists of the mature polypeptide of SEQ ID NO: 2 or SEQ ID NO: 4. In another preferred aspect, the mature polypeptide comprises or consists of amino acids 214 to 511 of SEQ ID NO: 2 or amino acids 214 to 517 of SEQ ID NO: 4.

The present invention also relates to isolated polypeptides having protease activity that are encoded by polynucleotides that hybridize under very low stringency conditions, low stringency conditions, medium stringency conditions, medium-high stringency conditions, high stringency conditions, or very high stringency conditions with (i) the mature polypeptide coding sequence of SEQ ID NO: 1 or 3, (ii) the genomic DNA sequence encoding the mature polypeptide coding sequence of SEQ ID NO: 1, or (iii) the full-length complementary strand of (i) or (ii) (J. Sambrook, E. F. Fritsch, and T. Maniatis, 1989, *Molecular Cloning, A Laboratory Manual,* 2d edition, Cold Spring Harbor, N.Y.).

The polynucleotide of SEQ ID NO: 1 or 3 or a subsequence thereof, as well as the amino acid sequence of SEQ ID NO: 2 or 4 or a fragment thereof, may be used to design nucleic acid probes to identify and clone DNA encoding polypeptides having protease activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length, Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having protease activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or 3 or a subsequence thereof, the carrier material is preferably used in a Southern blot.

For purposes of the present invention, hybridization indicates that the polynucleotide hybridizes to a labeled nucleic acid probe corresponding to the mature polypeptide coding sequence of SEQ ID NO: 1 or 3; the genomic DNA sequence comprising the mature polypeptide coding sequence of SEQ ID NO: 1 or 3; its full-length complementary strand; or a subsequence thereof; under very low to very high stringency conditions. Molecules to which the nucleic acid probe hybridizes under these conditions can be detected using, for example, X-ray film.

In one aspect, the nucleic acid probe is the mature polypeptide coding sequence of SEQ ID NO: 1. In another aspect, the nucleic acid probe is nucleotides 692 to 1585 of SEQ ID NO: 1, In one aspect, the nucleic acid probe is the mature polypeptide coding sequence of SEQ ID NO: 3. In another aspect, the nucleic acid probe is nucleotides 740 to 1651 of SEQ ID NO: 3. In another aspect, the nucleic acid probe is a polynucleotide that encodes the polypeptide of SEQ ID NO: 2 or 4 or a fragment thereof. In another preferred aspect, the nucleic acid probe is SEQ ID NO: 1 or 3.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The present invention relates to isolated polypeptides having protease activity encoded by polynucleotides having a sequence identity to the mature polypeptide coding sequence of SEQ ID NO: 1 of at least 60%, e.g., at least 65%, at least 70%, at least 75%, at least 80%, at least 85%, at least 90%, at least 95%, at least 96%, at least 97%, at least 98%, at least 99%, or 100%.

The present invention also relates to isolated polypeptides having protease activity encoded by polynucleotides having a sequence identity to the mature polypeptide coding sequence of SEQ ID NO: 3 of at least 60%, e.g., at least 65%, at least 70%, at least 75%, at least 80%, at least 85%, at least 90%, at least 95%, at least 96%, at least 97%, at least 98%, at least 99%, or 100%.

The present invention also relates to variants comprising a substitution, deletion, and/or insertion of one or more (or several) amino acids of the mature polypeptide of SEQ ID NO: 2 or 4, or a homologous sequence thereof. Preferably the variant has at least 60% sequence identity to the mature polypeptide of SEQ ID NO: 2 or SEQ ID NO: 4; e.g., at least 65%, at least 70%, at least 75%, at least 80%, at least 85%, at least 90%, at least 95%, at least 96%, at least 97%, at least 98%, at least 99%, but less than 100% identity to the mature polypeptide of SEQ ID NO: 2 or SEQ ID NO: 4.

Substantially homologous polypeptides of the sequences described above are characterized as having one or more (several) amino acid substitutions, deletions, and/or insertions in the mature polypeptide. Preferably, amino acid changes are of a minor nature, that is conservative amino acid substitutions or insertions that do not significantly affect the folding and/or activity of the protein; small deletions, typically of one to about nine amino acids, such as one, two, three, four, five, six, seven, eight or nine amino acids; preferably from one to about 15 amino acids, such as 10, 11, 12, 13, 14 or 15 amino acids; and most preferably from one to about 30 amino acids, such as 16, 17, 18, 19, 20, 21, 22, 23, 24, 25, 26, 27, 28, 29 or 30 amino acids; small amino- or carboxyl-terminal extensions, such as an amino-terminal methionine residue; a small linker peptide of up to about five to ten residues, preferably from 10 to 15 residues and most preferably from 20 to 25 residues, or a small extension that facilitates purification by changing net charge or another function, such as a poly-histidine tag, an antigenic epitope, protein A, a carbohydrate binding module or a another binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide. The catalytic residues may also be determined by alignment with known M4 metalloprotease where it has been found that the catalytic residues are conserved in all such proteases. In one embodiment essential amino acid residues determined by alignment with known M4 metalloproteases are Glu 350/E350) and His 435 (H435) of SEQ ID NO: 2 or Glu 358 (E358) and His 441 (H441) of SEQ ID NO: 4.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The total number of amino acid substitutions, deletions and/or insertions of the mature polypeptide of SEQ ID NO: 2 or 4 are not more than 10, e.g., 1, 2, 3, 4, 5, 6, 7, 8 or 9.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

The polypeptide may be hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of M4 Metalloproteases

A M4 Metalloprotease useful in the present invention may be obtained from microorganisms of any genus. For purposes of the present invention, the term "obtained from" as used herein in connection with a given source shall mean that the polypeptide encoded by a nucleotide sequence is produced by the source in which it is naturally present or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram-positive bacterial polypeptide such as an *Alicyclobacillus, Bacillus, Clostridium, Enterococcus, Geobacillus, Lactobacillus, Lactococcus, Oceanobacillus, Staphylococcus, Streptococcus*, or *Streptomyces* polypeptide having metalloprotease activity, or a gram-negative bacterial polypeptide such as a *Campylobacter, E. coli, Flavobacterium, Fusobacterium, Helicobacter, Ilyobacter, Neisseria, Pseudomonas, Salmonella, Ureaplasma* polypeptide.

In one aspect the polypeptide is an *Alicyclobacillus acidophilus, Alicyclobacillus acidoterrestris* or *Alicyclobacillus acidocaldarius* polypeptide.

In another aspect, the polypeptide is a *Bacillus alkalophilus, Bacillus amyloliquefaciens, Bacillus brevis, Bacillus cereus, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide.

In another aspect, the polypeptide is a *Geobacillus caldolyticus, Geobacillus stearothermophilus* polypeptide.

In another aspect, the polypeptide is a *Streptococcus equisimilis, Streptococcus pyogenes, Streptococcus uberis*, or *Streptococcus equi* subsp. *Zooepidemicus* polypeptide.

In another aspect, the polypeptide is a *Streptomyces achromogenes, Streptomyces avermitilis, Streptomyces coelicolor, Streptomyces griseus*, or *Streptomyces lividans* polypeptide.

A polypeptide of the present invention may also be a fungal polypeptide, and more preferably a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acremonium, Aspergillus, Aureobasidium, Chaetomium, Cryptococcus, Filibasidium, Fusarium, Humicola, Magnaporthe, Mucor, Myceliophthora, Neocallimastix, Neurospora, Paecilomyces, Penicillium, Piromyces, Poronia, Schizophyllum, Talaromyces, Thermoascus, Thielavia, Tolypocladium, Trichoderma* or *Verticillium* polypeptide.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Aspergillus terreus, Chaetomium globosum, Coprinus cinereus, Diplodia gossyppina, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Magnaporthe grisea, Mucor miehei, Myceliophthora thermophila, Neurospora crassa, Penicillium purpurogenum, Phanerochaete chrysosporium, Poronia punctata, Pseudoplectania nigrella, Thermoascus aurantiacus, Thielavia terrestris, Trichoderma harzianum, Trichoderma koningii, Trichoderma longibrachiatum, Trichoderma reesei, Trichoderma viride, Trichophaea saccata* or *Verticillium tenerum* polypeptide.

In a preferred aspect, the polypeptide is an *Alicyclobacillus* sp. polypeptide.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected e.g. with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Alicyclobacillus* or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1 or 3, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* crylIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242; 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coil* ribosomal RNA (rrnB).

Preferred terminators for filamentous fungal host cells are obtained from the genes for *Aspergillus nidulans* anthranilate synthase, *Aspergillus niger* glucoamylase, *Aspergillus* niger alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus steamthermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase. *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromagenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol,* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No. 9,* 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is an *Alicyclobacillus* cell.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides with protease activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Signal Peptide and Propeptide

The present invention also relates to an isolated polynucleotide encoding a signal peptide comprising or consisting of amino acids 1 to 25 of SEQ ID NO: 2 and amino acids 1 to 25 of SEQ ID NO 4. The present invention also relates to an isolated polynucleotide encoding a propeptide comprising or consisting of amino acids 26 to 213 of SEQ ID NO: 2 and amino acids 26 to 213 of SEQ ID NO 4. The present invention also relates to an isolated polynucleotides encoding a signal peptides and a propeptide comprising or consisting of amino acids 26 to 213 of SEQ ID NO: 2 and 26 to 213 of SEQ ID NO 4. The polynucleotides may further comprise a gene encoding a protein, which is operably linked to the signal peptide and/or propeptide. The protein is preferably foreign to the signal peptide and/or propeptide.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

The present invention is further described by the following examples that should not be construed as limiting the scope of the invention.

Compositions

The present invention also relates to compositions comprising a Metalloprotease of the invention. Preferably, the compositions are enriched in a Metalloprotease of the invention. The term "enriched" indicates that the protease activity of the composition has been increased.

In one embodiment, the present invention relates to compositions in particular to cleaning compositions and/or detergent compositions comprising a Metalloprotease of the invention and a suitable carrier and/or excipient.

In one embodiment, the detergent composition may be adapted for specific uses such as laundry, in particular household laundry, dish washing or hard surface cleaning.

The detergent compositions of the invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. The detergent compositions of the invention may find use in hard surface cleaning, automatic dishwashing applications, as well as cosmetic applications such as dentures, teeth, hair and skin.

In a preferred embodiment, the detergent compositions comprise one or more conventional carrier(s) and/or excipient(s) such as those exemplified below.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

Unless otherwise noted, all component or composition levels provided herein are made in reference to the active level of that component or composition, and are exclusive of impurities, for example, residual solvents or by-products, which may be present in commercially available sources.

The metalloproteases of the invention are normally incorporated in the detergent composition at a level of from 0.000001% to 2% of enzyme protein by weight of the composition, preferably at a level of from 0.00001% to 1% of enzyme protein by weight of the composition, more preferably at a level of from 0.0001% to 0.75% of enzyme protein by weight of the composition, even more preferably at a level of from 0.001% to 0.5% of enzyme protein by weight of the composition.

Furthermore, the metalloproteases of the invention are normally incorporated in the detergent composition in such amounts that their concentration in the wash water is at a level of from 0.0000001% to 1% enzyme protein, preferably at a level of from 0.000005% to 0.01% of enzyme protein, more preferably at a level of from 0.000001% to 0.005% of enzyme protein, even more preferably at a level of from 0.00001% to 0.001% of enzyme protein in wash water.

As is well known, the amount of enzyme will also vary according to the particular application and/or as a result of the other components included in the compositions.

A composition for use in automatic dishwash (ADW), for example, may include 0.001%-50%, such as 0.01%-25%, such as 0.02%-20%, such as 0.1-15% of enzyme protein by weight of the composition.

A composition for use in laundry granulation, for example, may include 0.0001%-50%, such as 0.001%-20%, such as 0.01%-15%, such as 0.05%-10% of enzyme protein by weight of the composition.

A composition for use in laundry liquid, for example, may include 0.0001%-10%, such as 0.001-7%, such as 0.1%-5% of enzyme protein by weight of the composition.

In some preferred embodiments, the detergent compositions provided herein are typically formulated such that, during use in aqueous cleaning operations, the wash water has a pH of from about 5.0 to about 11.5, or in alternative embodiments, even from about 6.0 to about 10.5, such as from about 5 to about 11, from about 5 to about 10, from about 5 to about 9, from about 5 to about 8, from about 5 to about 7, from about 6 to about 11, from about 6 to about 10, from about 6 to about 9, from about 6 to to about 8, from about 6 to about 7, from about 7 to about 11, from about 7 to about 10, from about 7 to about 9, or from about 7 to about 8. In some preferred embodiments, granular or liquid laundry products are formulated such that the wash water has a pH from about 5.5 to about 8. Techniques for controlling pH at recommended usage levels include the use of buffers, alkalis, acids, etc., and are well known to those skilled in the art.

Enzyme components weights are based on total active protein. All percentages and ratios are calculated by weight unless otherwise indicated. All percentages and ratios are calculated based on the total composition unless otherwise indicated. In the exemplified detergent composition, the enzymes levels are expressed by pure enzyme by weight of the total composition and unless otherwise specified, the detergent ingredients are expressed by weight of the total composition.

The enzymes of the present invention also find use in detergent additive products. A detergent additive product comprising a Metalloprotease of the invention is ideally suited for inclusion in a wash process when, e.g., temperature is low, the pH is between 6 and 8 and the washing time short, e.g., below 30 min.

The detergent additive product may be a Metalloprotease of the invention and preferably an additional enzyme. In one embodiment, the additive is packaged in dosage form for addition to a cleaning process. The single dosage may comprise a pill, tablet, gelcap or other single dosage unit including powders and/or liquids. In some embodiments, filler and/or carrier material(s) are included, suitable filler or carrier materials include, but are not limited to, various salts of sulfate, carbonate and silicate as well as talc, clay and the like. In some embodiments filler and/or carrier materials for liquid compositions include water and/or low molecular weight primary and secondary alcohols including polyols and diols. Examples of such alcohols include, but are not limited to, methanol, ethanol, propanol and isopropanol.

In one particularly preferred embodiment the metalloprotease according to the invention is employed in a granular composition or liquid, the metalloprotease may be in form of an encapsulated particle. In one embodiment, the encapsulating material is selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof.

The compositions according to the invention typically comprise one or more detergent ingredients. The term detergent compositions include articles and cleaning and treatment compositions. The term cleaning composition includes, unless otherwise indicated, tablet, granular or powder-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use. The composition can also be in unit dose packages, including those known in the art and those that are water soluble, water insoluble and/or water permeable.

In embodiments in which cleaning and/or detergent components may not be compatible with the metalloprotease of the present invention, suitable methods may be used for keeping the cleaning and/or detergent components and the metalloprotease separated (i.e., not in contact with each other) until combination of the two components is appropriate. Such separation methods include any suitable method known in the art (e.g., gelcaps, encapsulation, tablets, physical separation).

As mentioned when the metalloprotease of the invention is employed as a component of a detergent composition (e.g., a laundry washing detergent composition, or a dishwashing detergent composition), it may, for example, be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly (ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)). The enzymes of the detergent compositions of the invention may also be stabilized using conventional stabilizing agents such as polyol, e.g., propylene glycol or glycerol, a sugar or sugar alcohol, lactic acid, and the composition may be formulated as described in, e.g., WO 92/19709 and WO 92/19708. The enzymes of the invention may also be stabilized by adding reversible enzyme inhibitors, e.g., of the protein type (as described in EP 0 544 777 B1) or the boronic acid type. Other enzyme stabilizers are well known in the art, such as peptide aldehydes and protein hydrolysate, e.g. the metalloproteases according to the invention may be stabilized using peptide aldehydes or ketones such as described in WO 2005/105826 and WO 2009/118375.

Protected enzymes for inclusion in a detergent composition of the invention may be prepared, as mentioned above, according to the method disclosed in EP 238 216.

The composition may be augmented with one or more agents for preventing or removing the formation of the biofilm. These agents may include, but are not limited to, dispersants, surfactants, detergents, other enzymes, antimicrobials, and biocides.

Other Enzymes

In one embodiment, a metalloprotease of th invention is combined with one or more enzymes, such as at least two enzymes, more preferred at least three, four or five enzymes. Preferably, the enzymes have different substrate specificity, e.g., proteolytic activity, amylolytic activity, lipolytic activity, hemicellulytic activity or pectolytic activity.

The detergent additive as well as the detergent composition may comprise one or more enzymes such as a protease, lipase, cutinase, an amylase, carbohydrase, cellulase, pectinase, mannanase, arabinase, galactanase, xylanase, oxidase, e.g., a laccase and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of animal, vegetable or microbial origin. Particularly suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691, 178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 99/01544.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in U.S. Pat. No. 7,262,042 and WO 2009/021867, and subtilisin lentus, subtilisin Novo, subtilisin Carlsberg, *Bacillus licheniformis*, subtilisin BPN', subtilisin 309, subtilisin 147 and subtilisin 168 described in WO 89/06279 and protease PD138 described in (WO 93/18140). Other useful proteases may be those described in WO 92/175177, WO 01/16285, WO 02/26024 and WO 02/16547. Examples of trypsin-like proteases are trypsin (e.g. of porcine or bovine origin) and the *Fusarium* protease described in WO 89/06270, WO 94/25583 and WO 2005/040372, and the chymotrypsin proteases derived from *Cellulomonas* described in WO 2005/052161 and WO 2005/052146.

A further preferred protease is the alkaline protease from *Bacillus lentus* DSM 5483, as described for example in WO 95/23221, and variants thereof which are described in WO 92/21760, WO 95/23221, EP 1921147 and EP 1921148.

Examples of metalloproteases are the neutral metalloprotease as described in WO07/044993 (Genencor Int.) such as those derived from *Bacillus amyloliquefaciens*. Examples of useful proteases are the variants described in: WO 92/19729, WO 96/034946, WO 98/20115, WO 98/20116, WO 99/11768, WO 01/44452, WO 03/006602, WO 2004/003186, WO 2004/041979, WO 2007/006305, WO 2011/036263, WO 2011/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the protease variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases: Suitable lipases include those of animal, vegetable or microbial origin. Particularly suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipolase Ultra™, and Lipex™ (Novozymes A/S).

Amylases: Suitable amylases which can be used together with the metalloprotease of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839. Suitable amylases include amylases having SEQ ID NO: 3 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H 156, A181, N 190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184. Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476. More preferred variants are those having a deletion in positions 181 and 182 or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476. Other amylases which can be used are amylases having SEQ ID NO: 2 of WO 2008/153815, SEQ ID NO: 10 in WO 01/66712 or variants thereof having 90% sequence identity to SEQ ID NO: 2 of WO 2008/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264. Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+G475K;
S125A+N 128C+K178L+T182G+Y305R+G475K; or
S125A+N128C+T131I+T165I+K178L+T182G+Y305R+G475K' wherein the variants are C-terminally truncated and optionally further comprises a substitution at position 243 and/or a deletion at position 180 and/or position 181. Other suitable amylases are the alpha-amylase having SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO 01/66712: R28, R118, N174, R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions. Other examples are amylase variants such as those described in WO 2011/098531, WO 2013/001078 and WO 2013/001087, Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates as described above, liquids, in particular stabilized liquids, or slurries.

Surfactants

Typically, the detergent composition comprises (by weight of the composition) one or more surfactants in the range of 0% to 50%, preferably from 2% to 40%, more preferably from 5% to 35%, more preferably from 7% to 30%, most preferably from 10% to 25%, even most preferably from 15% to 20%. In a preferred embodiment the detergent is a liquid or powder detergent comprising less than 40%, preferably less than 30%, more preferably less than 25%, even more preferably less than 20% by weight of surfactant. The composition may comprise from 1% to 15%, preferably from 2% to 12%, 3% to 10%, most preferably from 4% to 8%, even most preferably from 4% to 6% of one or more surfactants. Preferred surfactants are anionic surfactants, non-ionic surfactants, cationic surfactants, zwitterionic surfactants, amphoteric surfactants, and mixtures thereof. Preferably, the major part of the surfactant is anionic. Suitable anionic surfactants are well known in the art and may comprise fatty acid carboxylates (soap), branced-chain, linear-chain and random chain alkyl sulfates or fatty alcohol sulfates or primary alcohol sulfates or alkyl benzenesulfonates such as LAS and LAB or phenylalknesulfonates or alkenyl sultanates or alkenyl benzenesulfonates or alkyl ethoxysulfates or fatty alcohol ether sulfates or alpha-olefin sulfonate or dodecenyl/tetradecnylsuccinic acid. The anionic surfactants may be alkoxylated. The detergent composition may also comprise from 1 wt % to 10 wt % of non-ionic surfactant, preferably from 2 wt % to 8 wt %, more preferably from 3 wt % to 7 wt %, even more preferably less than 5 wt % of non-ionic surfactant. Suitable non-ionic surfactants are well known in the art and may comprise alcohol ethoxylates, and/or alkyl ethoxylates, and/or alkylphenol ethoxylates, and/or glucamides such as fatty acid N-glucosyl N-methyl amides, and/or alkyl polyglucosides and/or mono- or diethanolamides or fatty acid amides. The detergent composition may also comprise from 0 wt % to 10 wt % of cationic surfactant, preferably from 0.1 wt % to 8 wt %, more preferably from 0.5 wt % to 7 wt %, even more preferably less than 5 wt % of cationic surfactant. Suitable cationic surfactants are well known in the art and may comprise alkyl quaternary ammonium compounds, and/or alkyl pyridinium compounds and/or alkyl quaternary phosphonium compounds and/or alkyl ternary sulphonium compounds. The composition preferably comprises surfactant in an amount to provide from 100 ppm to 5,000 ppm surfactant in the wash liquor during the laundering process. The composition upon contact with water typically forms a wash liquor comprising from 0.5 g/l to 10 g/l detergent composition. Many suitable surface active compounds are available and fully described in the literature, for example, in "Surface-Active Agents and Detergents", Volumes I and 11, by Schwartz, Perry and Berch.

Builders

The main role of builder is to sequester divalent metal ions (such as calcium and magnesium ions) from the wash solution that would otherwise interact negatively with the surfactant system. Builders are also effective at removing metal ions and inorganic soils from the fabric surface, leading to improved removal of particulate and beverage stains. Builders are also a source of alkalinity and buffer the pH of the wash water to a level of 9.5 to 11. The buffering capacity is also termed reserve alkalinity, and should preferably be greater than 4.

The detergent compositions of the present invention may comprise one or more detergent builders or builder systems. Many suitable builder systems are described in the literature, for example in Powdered Detergents, Surfactant science series volume 71, Marcel Dekker, Inc. Builder may comprise from 0% to 60%, preferably from 5% to 45%, more preferably from 10% to 40%, most preferably from 15% to 35%, even more preferably from 20% to 30% builder by weight of the subject composition. The composition may comprise from 0% to 15%, preferably from 1% to 12%, 2% to 10%, most preferably from 3% to 8%, even most preferably from 4% to 6% of builder by weight of the subject composition.

Builders include, but are not limited to, the alkali metal, ammonium and alkanolammonium salts of polyphosphates (e.g., tripolyphosphate STPP), alkali metal silicates, alkaline earth and alkali metal carbonates, aluminosilicate builders (e.g., zeolite) and polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Ethanole amines (MEA, DEA, and TEA) may also contribute to the buffering capacity in liquid detergents.

Bleaches

The detergent compositions of the present invention may comprise one or more bleaching agents. In particular powdered detergents may comprise one or more bleaching agents. Suitable bleaching agents include other photobleaches, pre-formed peracids, sources of hydrogen peroxide, bleach activators, hydrogen peroxide, bleach catalysts and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) other photobleaches for example Vitamin K3;

(2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxone, and mixtures thereof. Suitable percarboxylic acids include hydrophobic and hydrophilic peracids having the formula R—(C═O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include inorganic salts such as alkali metal silicate, carbonate or borate salts or mixtures thereof, or organic materials such as water-soluble or dispersible polymers, waxes, oils or fatty soaps. Useful bleaching compositions are described in U.S. Pat. Nos. 5,576,282, and 6,306,812;

(4) bleach activators having R—(C═O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof; and (5) bleach catalysts that are capable of accepting an oxygen atom from peroxyacid and transferring the oxygen atom to an oxidizable substrate are described in WO 2008/007319. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof. The bleach catalyst will typically be comprised in the detergent composition at a level of from 0.0005% to 0.2%, from 0.001% to 0.1%, or even from 0.005% to 0.05% by weight.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Adjunct Materials

Dispersants—The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents—The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent—The detergent compositions of the present invention will preferably also contain additional components that may tint articles being cleaned, such as fluorescent whitening agent or optical brighterners. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino)stilbene-2,2'-disulphonate, 4,4'-bis-(2,4-dianilino-s-triazin-6-ylamino)stilbene-2,2'-disulphonate, 4,4'-bis-(2-anilino-4(N-methyl-N-2-hydroxy-ethylamino)-s-triazin-6-ylamino)stilbene-2,2'-disulphonate, 4,4'-bis-(4-phenyl-2,1,3-triazol-2-yl)stilbene-2,2'-disulphonate, 4,4'-bis-(2-anilino-4(1-methyl-2-hydroxy-ethylamino)-s-triazin-6-ylamino) stilbene-2,2'-disulphonate and 2-(stilbyl-4"-naptho-1,2':4,5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino)stilbene disulphonate. Tinopal CBS is the disodium salt of 2,2'-bis-(phenyl-styryl)disulphonate.

Also preferred are fluorescent whitening agents is the commercially available Parawhite KX, supplied by Paramount Minerals and Chemicals, Mumbai, India.

Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Fabric hueing agents—The detergent compositions of the present invention may also include fabric hueing agents such as dyes or pigments which when formulated in detergent compositions can deposit onto a fabric when said fabric is contacted with a wash liquor comprising said detergent compositions thus altering the tint of said fabric through absorption of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1 876 226. The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch.

Soil release polymers—The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series, volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523. Furthermore random graft co-polymers are suitable soil release polymers Suitable graft co-polymers are described in more detail in WO 2007/138054, WO 2006/108856 and WO 2006/113314. Other soil release polymers are substituted polysaccharide structures especially substituted cellulosic structures such as modified cellulose deriviatives such as those described in EP 1 867 808 or WO 2003/040279. Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents—The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, structurants for liquid detergents and/or structure elasticizing agents.

In one aspect the detergent is a compact fluid laundry detergent composition comprising: a) at least about 10%, preferably from 20 to 80% by weight of the composition, of surfactant selected from anionic surfactants, non ionic surfactants, soap and mixtures thereof; b) from about 1% to about 30%, preferably from 5 to 30%, by weight of the composition, of water; c) from about 1% to about 15%, preferably from 3 to 10% by weight of the composition, of non-aminofunctional solvent; and d) from about 5% to about 20%, by weight of the composition, of a performance additive selected from chelants, soil release polymers, enzymes and mixtures thereof; wherein the compact fluid laundry detergent composition comprises at least one of: (i) the surfactant has a weight ratio of the anionic surfactant to the nonionic surfactant from about 1.5:1 to about 5:1, the surfactant comprises from about 15% to about 40%, by weight of the composition, of anionic surfactant and comprises from about 5% to about 40%, by weight of the composition, of the soap; (ii) from about 0.1% to about 10%, by weight of the composition, of a suds boosting agent selected from suds boosting polymers, cationic surfactants, zwitterionic surfactants, amine oxide surfactants, amphoteric surfactants, and mixtures thereof; and (ii) both (i) and (ii). All the ingredients are described in WO 2007/130562. Further polymers useful in detergent formulations are described in WO 2007/149806.

In another aspect the detergent is a compact granular (powdered) detergent comprising a) at least about 10%, preferably from 15 to 60% by weight of the composition, of surfactant selected from anionic surfactants, non ionic surfactants, soap and mixtures thereof; b) from about 10 to 80% by weight of the composition, of a builder, preferably from 20% to 60% where the builder may be a mixture of builders selected from i) phosphate builder, preferably less than 20%, more preferably less than 10% even more preferably less than 5% of the total builder is a phosphate builder; ii) a zeolite builder, preferably less than 20%, more preferably less than 10% even more preferably less than 5% of the total builder is a zeolite builder; iii) citrate, preferably 0 to 5% of the total builder is a citrate builder; iv) polycarboxylate, preferably 0 to 5% of the total builder is a polycarboxylate builder; v) carbonate, preferably 0 to 30% of the total builder is a carbonate builder; and vi) sodium silicates, preferably 0 to 20% of the total builder is a sodium silicate builder; c) from about 0% to 25% by weight of the composition, of fillers such as sulphate salts, preferably from 1% to 15%, more preferably from 2% to 10%, more preferably from 3% to 5% by weight of the composition, of fillers; and d) from about 0.1% to 20% by weight of the composition, of enzymes, preferably from 1% to 15%, more preferably from 2% to 10% by weight of the composition, of enzymes.

Use of M4 Metalloproteases in Detergents

The soils and stains that are important for detergent formulators are composed of many different substances, and a range of different enzymes, all with different substrate specificities have been developed for use in detergents both in relation to laundry and hard surface cleaning, such as dishwashing. These enzymes are considered to provide an enzyme detergency benefit, since they specifically improve stain removal in the cleaning process they are applied in as compared to the same process without enzymes. Stain removing enzymes that are known in the art include enzymes such as carbohydrases, amylases, proteases, lipases, cellulases, hemicellulases, xylanases, cufinases, and pectinase.

In one aspect, the present invention concerns the use of metalloproteases of the invention in detergent compositions and cleaning processes, such as laundry and hard surface cleaning. Thus, in one aspect, the present invention demonstrates the detergency effect of the metalloproteases of the invention on various stains and under various conditions. In a particular aspect of the invention the detergent composition and the use in cleaning process concerns the use of a metalloprotease of the invention together with at least one of the above mentioned stain removal enzymes, such as another protease, and in particular a serine protease.

In a preferred aspect of the present invention the metalloproteases of the invention useful according to the invention may be combined with at least two enzymes. These additional enzymes are described in details in the section "other enzymes", more preferred at least three, four or five enzymes. Preferably, the enzymes have different substrate specificity, e.g., carbolytic activity, proteolytic activity, amylolytic activity, lipolytic activity, hemicellulytic activity or pectolytic activity. The enzyme combination may for example be a metalloprotease of the invention with another stain removing enzyme, e.g., a metalloprotease of the invention and a protease, a metalloprotease of the invention and an amylase, a metalloprotease of the invention and a cellulase, a metalloprotease of the invention and a hemicellulase, a metalloprotease of the invention and a lipase, a metalloprotease of the invention and a cutinase, a metalloprotease of the invention and a pectinase or a metalloprotease of the invention and an anti-redeposition enzyme. More preferably, the metalloprotease of the invention is combined with at least two other stain removing enzymes, e.g., a metalloprotease of the invention, a lipase and an amylase; or a metalloprotease of the invention, a protease and an amylase; or a metalloprotease of the invention, a protease and a lipase; or a metalloprotease of the invention, a protease and a pectinase; or a metalloprotease of the invention, a protease and a cellulase; or a metalloprotease of the invention, a protease and a hemicellulase; or a metalloprotease of the invention, a protease and a cutinase; or a metalloprotease of the invention, an amylase and a pectinase; or a metalloprotease of the invention, an amylase and a cutinase; or a metalloprotease of the invention, an amylase and a cellulase; or a metalloprotease of the invention, an amylase and a hemicellulase; or a metalloprotease of the invention, a lipase and a pectinase; or a metalloprotease of the invention, a lipase and a cutinase; or a metalloprotease of the invention, a lipase and a cellulase; or a metalloprotease of the invention, a lipase and a hemicellulase. Even more preferably, a metalloprotease of the invention may be combined with at least three other stain removing enzymes, e.g., a metalloprotease of the invention, a protease, a lipase and an amylase; or a metalloprotease of the invention, a protease, an amylase and a pectinase; or a metalloprotease of the invention, a protease, an amylase and a cutinase; or a metalloprotease of the invention, a protease, an amylase and a cellulase; or a metalloprotease of the invention, a protease, an amylase and a hemicellulase; or a metalloprotease of the invention, an amylase, a lipase and a pectinase; or a metalloprotease of the invention, an amylase, a lipase and a cutinase; or a metalloprotease of the invention, an amylase, a lipase and a cellulase; or a metalloprotease of the invention, an amylase, a lipase and a hemicellulase; or a metalloprotease of the invention, a protease, a lipase and a pectinase; or a metalloprotease of the invention, a protease, a lipase and a cutinase; or a metalloprotease of the invention, a protease, a lipase and a cellulase; or a metalloprotease of the invention, a protease, a lipase and a hemicellulase. A metalloprotease according to the present invention may be combined with any of the enzymes selected from the non-exhaustive list comprising: carbohydrases, such as an amylase, a hemicellulase, a pectinase, a cellulase, a xanthanase or a pullulanase, a peptidase, a protease or a lipase.

In a preferred embodiment, a metalloprotease of the invention is combined with a serine protease, e.g., an S8 family protease such as as Savinase® or a variant hereof.

In another embodiment of the present invention, a metalloprotease of the invention useful according to the present invention may be combined with one or more other metalloproteases, such as another M4 Metalloprotease, including Neutrase® or Thermolysin. Such combinations may further comprise combinations of the other detergent enzymes as outlined above.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one metalloprotease of the invention. The cleaning process or a textile care process can for example be carried out in a machine washing process or in a manual washing process. The washing solution can for example be an aqueous washing solution containing a detergent composition.

The fabrics and/or garments subjected to a washing, cleaning or textile care process of the present invention may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

The invention further concerns the use of metalloprotease of the invention in a proteinaceous stain removing processes. The proteinaceous stains may be stains such as food stains, e.g., baby food, sebum, cocoa, egg, blood, milk, ink, grass, or a combination hereof.

Typical detergent compositions includes various components in addition to the enzymes, these components have different effects, some components like the surfactants lower the surface tension in the detergent, which allows the stain being cleaned to be lifted and dispersed and then washed away, other components like bleach systems removes discolor often by oxidation and many bleaches also have strong bactericidal properties, and are used for disinfecting and sterilizing. Yet other components like builder and chelator softens, e.g., the wash water by removing the metal ions form the liquid.

In a particular embodiment, the invention concerns the use of a composition comprising a metalloprotease of the invention, wherein said enzyme composition further comprises at least one or more of the following a surfactant, a builder, a chelator or chelating agent, bleach system or bleach component in laundry or dish wash.

In a preferred embodiment of the invention the amount of a surfactant, a builder, a chelator or chelating agent, bleach system and/or bleach component are reduced compared to amount of surfactant, builder, chelator or chelating agent, bleach system and/or bleach component used without the added metalloprotease of the invention. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of metalloprotease of the invention, such as a conventional amount of such component. In one aspect, the metalloprotease of the invention is used in detergent compositions wherein said composition is free of at least one component which is a surfactant, a builder, a chelator or chelating agent, bleach system or bleach component and/or polymer.

Washing Method

The detergent compositions of the present invention are ideally suited for use in laundry applications. Accordingly, the present invention includes a method for laundering a fabric. The method comprises the steps of contacting a fabric to be laundered with a cleaning laundry solution comprising the detergent composition according to the invention. The fabric may comprise any fabric capable of being laundered in normal consumer use conditions. The solution preferably has a pH of from about 5.5 to about 8. The compositions may be employed at concentrations of from about 100 ppm, preferably 500 ppm to about 15,000 ppm in solution. The water temperatures typically range from about 5° C. to about 90° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

The present invention relates to a method of cleaning a fabric, a dishware or hard surface with a detergent composition comprising a metalloprotease of the invention.

A preferred embodiment concerns a method of cleaning, said method comprising the steps of: contacting an object with a cleaning composition comprising a metalloprotease of the invention under conditions suitable for cleaning said object. In a preferred embodiment the cleaning composition is a detergent composition and the process is a laundry or a dish wash process.

Still another embodiment relates to a method for removing stains from fabric which comprises contacting said a fabric with a composition comprising a metalloprotease of the invention under conditions suitable for cleaning said object.

In a preferred embodiment the compositions for use in the methods above further comprises at least one additional enzyme as set forth in the "other enzymes" section above, such as an enzyme selected from the group consisting of carbohydrases, peptidases, proteases, lipases, cellulase, xylanases or cutinases or a combination hereof. In yet another preferred embodiment the compositions comprises a reduced amount of at least one or more of the following components a surfactant, a builder, a chelator or chelating agent, bleach system or bleach component or a polymer.

Low Temperature Uses

As previously stated, the metalloprotease of the invention are M4 Metalloproteases. The M4 Metalloproteases have also been termed the Thermolysin family because the M4 metalloprotease known as "Thermolysin" was the first characterized M4 metalloproteases and is one of the best characterized. The Thermolysins are known for their high temperature performance. High temperature performance is preferred, e.g., in processes for protein synthesis where the Thermolysins have been frequently used. Thus since the high temperature performance is advantageous in these processes thermostable variants of several Thermolysins have been made.

It was surprising, therefore, that some of the M4 metalloproteases—e.g., the metalloprotease of the invention—actually perform relatively better at low temperature, e.g., temperatures of about 40° C. or below than at higher temperatures, e.g., of about 60° C. or above when tested in e.g. AMSA.

Moreover, in a particularly preferred embodiment the metalloproteases of the invention perform relatively better on at least some stains than a commercial metalloprotease such as Neutrase® at a wash temperature of about 40° C. or below when tested in AMSA.

Thus, one embodiment of the invention concerns a method of doing laundry, dish wash or industrial cleaning comprising contacting a surface to be cleaned with a metalloprotease of the invention, and wherein said laundry, dish wash, industrial or institutional cleaning is performed at a temperature of about 40° C. or below. One embodiment of the invention relates to the use of a metalloprotease in laundry, dish wash or a cleaning process wherein the temperature in laundry, dish wash, industrial cleaning is about 40° C. or below In another embodiment, the invention concerns the use of a metalloprotease in a protein removing process, wherein the temperature in the protein removing process is about 40° C. or below.

The present invention also relates to the use in laundry, dish wash or industrial cleaning process of a metalloprotease having at least one improved property compared to a commercial metalloprotease such as Neutrase® and wherein the temperature in laundry, dish wash or cleaning process is performed at a temperature of about 40° C. or below.

In each of the above-identified methods and uses, the wash temperature is about 40° C. or below, such as about 39° C. or below, such as about 38° C. or below, such as about 37° C. or below, such as about 36° C. or below, such as about 35° C. or below, such as about 34° C. or below, such as about 33° C. or below, such as about 32° C. or below, such as about 31° C. or below, such as about 30° C. or below, such as about 29° C. or below, such as about 28° C. or below, such as about 27° C. or below, such as about 26° C. or below, such as about 25° C. or below, such as about 24° C. or below, such as about 23° C. or below, such as about 22° C. or below, such as about 21° C. or below, such as about 20° C. or below, such as about 19° C. or below, such as about 18° C. or below, such as about 17° C. or below, such as about 16° C. or below, such as about 15° C. or below, such as about 14° C. or below, such as about 13° C. or below, such as about 12° C. or below, such as about 11° C. or below, such as about 10° C. or below, such as about 9° C. or below, such as about 8° C. or below, such as about 7° C. or below, such as about 6° C. or below, such as about 5° C. or below, such as about 4° C. or below, such as about 3° C. or below, such as about 2° C. or below, such as about 1° C. or below.

In another preferred embodiment, the wash temperature is in the range of about 5-40° C., such as about 5-30° C., about 5-20° C., about 5-10° C., about 10-40° C., about 10-30° C., about 10-20° C., about 15-40° C., about 15-30° C., about 15-20° C., about 20-40° C., about 20-30° C., about 25-40° C., about 25-30° C., or about 30-40° C. In a particular preferred embodiment the wash temperature is about 30° C.

In particular embodiments, the low temperature washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8.

In particular embodiments, the low temperature washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

Use in Removing Egg Stains

Another particular embodiment of the invention concerns removal of egg stains. These types of stain are often very difficult to remove completely. Egg stains are particularly problematic in hard surface cleaning such as dish wash where the stains often remain on the plates and cutlery after washing. The metalloproteases of the invention are particularly suitable for removing egg stains.

Thus, the invention further concerns methods for removing egg stains from textiles, fabrics and/or hard surfaces like dishes and cutlery in particular from fabrics and textiles. A preferred aspect of the invention concerns a method of removing egg stains from textiles and/or fabrics comprising contacting a surface in need of removal of an egg stain with a metalloprotease of the invention. In one embodiment, the invention comprises a method of removing egg stains from textiles and/or fabrics comprising contacting a surface in need of removal of an egg stain with a detergent composition comprising a metalloprotease of the invention. The invention also concerns a method of removing egg stains comprising adding a metalloprotease of the invention to a laundry and/or washing process wherein said textiles and/or fabric comprises various egg stains.

One embodiment of the present invention relates to a method for removal of egg stains from a hard surface or from laundry, the method comprising contacting the egg stain-containing hard surface or the egg stain-containing laundry with a cleaning or detergent composition, preferably a laundry or dish wash composition, containing a metalloprotease of the invention.

Another embodiment relates a method for removing egg stains from fabric or textile which comprises contacting the fabric or textile with a cleaning or detergent composition, preferably a laundry or dish wash composition, comprising a metalloprotease of the invention.

A still further embodiment relates to a method for removing egg stains from fabric or textile which comprises contacting said a fabric or textile with a composition comprising a metalloprotease of the invention, wherein said composition further comprises at least one additional enzyme as set forth in the "other enzymes" section above, such as an enzyme selected from the group consisting of a carbohydrase, a peptidase, a protease, a lipase, a cellulase, a xylanase, a cutinase or a combination hereof.

In particular embodiments, the egg removing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5, to about 7, about 6 to about 11, about 6 to about 10, about 6 to about 9, about 6 to to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8.

In particular embodiments, the egg removing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

All documents cited herein are incorporated by reference in the entirety.

The present invention is further described by the following examples that should not be construed as limiting the scope of the invention.

EXAMPLES

Materials and Methods
Protazyme AK Activity Assay:
Substrate: Protazyme AK tablet (AZCL-casein, Megazyme T-PRAK 1000).
Temperature: 37° C.
Assay buffer: 50 mM HEPES/NaOH, pH 7.0.

A Protazyme AK tablet is suspended in 2.0 ml 0.01% Triton X-100 by gentle stirring. 500 µl of this suspension and 500 µl assay buffer are dispensed in an Eppendorf tube and placed on ice. 20 µl protease sample (diluted in 0.01% Triton X-100) is added to the ice cold tube. The assay is initiated by transferring the Eppendorf tube to an Eppendorf thermomixer, which is set to the assay temperature. The tube is incubated for 15 minutes on the Eppendorf thermomixer at its highest shaking rate (1400 rpm). The incubation is stopped by transferring the tube back to the ice bath. Then the tube is centrifuged in an ice cold centrifuge for a few minutes and 200 µl supernatant is transferred to a microtiter plate. $OD_{650}$ was read as a measure of protease activity. A buffer blind is included in the assay (instead of enzyme).

Automatic Mechanical Stress Assay (AMSA) for Laundry

In order to assess the wash performance in laundry washing experiments are performed, using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner. For further description see WO 02/42740 especially the paragraph "Special method embodiments" at page 23-24.

The laundry experiments are conducted under the experimental conditions specified below:

| | |
|---|---|
| Detergent dosage | 2 g/L and 8 g/L (Laundry Liquid Model Detergent) |
| Enzyme dosage | 30 nM |
| Test solution volume | 160 microliters (140 microliters detergent and 20 microliters enzyme per slot) |
| pH | Adjusted to pH 7 or pH 6 (Laundry Liquid Model Detergent) |
| Wash time | 20 minutes |
| Temperature | 20° C. and 40° C. |
| Water hardness | 15° dH |

Model detergent and test materials are as follows:

| | |
|---|---|
| Laundry Liquid Model Detergent | NaOH 2.95% |
| | LAS acid: 11.52% |
| | Fatty acid (Soy C18): 5.5% |
| | MPG 5.05% |
| | C13-alkoholethoxylate, 7-8 EO: 9.45% |
| | Dequest 2066 C2 (Phosphonate): 1.00% |
| | TEA, Triethanolamin: 2.0% |
| | Fatty Acid (Coco C12): 4.5% |
| | Natrium citrate, dihydrate: 1.0% |
| | Ethanol (99%): 4.63% |
| | Opacifier (Syntran 5909): 0.12% |
| | Water ad 100% |
| Test Material | PC-05 (Blood/milk/ink on cotton/polyester) |
| | PC-03 (Chokolate-milk/soot on cotton/polyester) |
| | C-10 (Oil/milk/pigment on cotton) |
| | CS-37 (Full egg/pigment on cotton) |

All test materials are obtained from EMPA Testmaterials AG Mövenstrasse 12, CH-9015 St. Gallen, Switzerland, from Center For Testmaterials BV, P.O. Box 120, 3133 KT Vlaardingen, the Netherlands, and WFK Testgewebe GmbH, Christenfeld 10, D-41379 Brüggen, Germany.

Water hardness is adjusted to 15° dH by addition of $CaCl_2$, $MgCl_2$, and $NaHCO_3$ ($Ca^{2+}$:$Mg^{2+}$:$NaHCO_3$=4:1:7.5) to the test system. After washing the textiles were flushed in tap water and dried.

The wash performance is measured as the brightness of the color of the textile washed. Brightness can also be expressed as the intensity of the light reflected from the sample when illuminated with white light. When the sample is stained the intensity of the reflected light is lower than that of a clean sample. Expressed another way, a cleaner sample will reflect more light and will have a higher intensity. Therefore the intensity of the reflected light can be used to measure wash performance.

Color measurements are made with a professional flatbed scanner (Kodak iQsmart, Kodak, Midtager 29, DK-2605 Brøndby, Denmark), which is used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int=\sqrt{r^2+g^2+b^2}.$$

Example 1. Sequencing the *Alicyclobacillus* sp. O2525 Genome

A novel bacterial strains designated *Alicyclobacillus* sp. O2525 representing a new species within the genus *Alicyclobacillus* was isolated from an environmental sample collected in a Danish forest.

Chromosomal DNA of the strain was isolated by QIAamp DNA Blood Mini Kit" (Qiagen, Hilden, Germany). 2 ug of chromosomal DNA was subjected to partial shotgun genome sequencing, a service that is commercially available at FASTERIS SA, Switzerland. The genome sequence was analyzed for protein sequences encoding M4 metalloproteases and two genes encoding M4 metalloproteases were identified (SEQ ID NO: 1 and SEQ ID NO: 3).

Example 2. Construction of *Bacillus* Expression Vector Containing *Alicyclobacillus* sp. O2525 Genomic Sequence Encoding the M4 Metalloprotease Polypeptide of SEQ ID NO: 2

Cloning and Expression of Protease

The signal peptide from the alkaline protease from *B. clausii* (aprH) was fused by SOE PCR fusion as described in WO 99/43835 (hereby incorporated by reference) in frame to the DNA encoding the protease. To amplify the coding DNA, genomic DNA of *Alicyclobacillus* sp. O2525 was used as template and the oligomers C25DU.f and C25DU.r to amplify the gene by PCR, where the underlines sequences corresponds to the gene sequence, and the not underlined sequence correspond to the SOE expression cassette.

```
C25DU.f
                                           (SEQ ID NO: 5)
GTTCATCGATCGCATCGGCTGCTGTCACCGACAAGCAA

C25DU.r
                                           (SEQ ID NO: 6)
CCAAGGCCGGTTTTTTATGTTTTAGTTGACGCCTACGTT
```

The PCR reaction mixture had following composition:
1 µl Genomic *Alicyclobacillus* sp. O2525 DNA (10.4 ng/µl)
1 µl Primer C25DU.f (50 pmol/µl)
1 µl Primer C25DU.r (50 pmol/µl)
2 µl dNTP (10 mM)
10 µl Buffer HF (5×)
0.5 µl Phusion polymerase
34.5 µl water.

The Phusion polymerase and the Buffer HF was provided from Finnzymes and used according to the manufacturers instructions.

The PCR reaction mixture was subjected to a programme of
1. 98° C. for 30 min.
2. 98° C. for 10 s
3. 60° C. for 20 s
4. 72° C. for 2 min
5. Steps 2 to 4 was repeated 35 times
6. 72° C. for 10 min
7. Soak at 4° C.

The reaction mixture was loaded on a TAE agarosegel and a band in the expected size was observed.

The derived PCR product was fused to expression cassette elements. The protease gene from *Alicyclobacillus* sp. was expressed by control of a triple promoter system consisting of the promoters from *Bacillus licheniformis* alpha-amylase gene (amyL), *Bacillus amyloliquefaciens* alpha-amylase gene (amyQ), and the *Bacillus thuringiensis* crylIIA promoter including stabilizing sequence. The expression cassette has been described in WO 99/43835. Furthermore, the expression cassette contained a terminator (term) sequence and a gene coding for chloramphenicol acetyltransferase (cam) which was used as selection maker (as described in (Diderichsen et al., 1993, *Plasmid* 30: 312-315) for *B. subtilis*.

The fused gene fragment that was part of the the complete expression cassette described above was transformed into *B. subtilis* and the protease gene was integrated into the *Bacillus subtilis* chromosome by homologous recombination into the pectate lyase gene locus (WO 99/43835).

Chloramphenicol resistant transformants were analyzed by DNA sequencing to verify the correct DNA sequence of the construct.

Transformants were plated on LB+ 6 µg/ml Chloramplenicom+skimmed milk at 37° C. over night. Clearing halos were observed around the colonies indicating that the colonies produced active protease, whereas controls without the *Alicyclobacillus* sp. Metalloprotease gene did not give any halos.

Example 3. Characterization of the *Alicyclobacillus* sp. Genomic Sequence Having SEQ ID NO: 1 and Encoding a Polypeptide Having Protease Activity DNA sequencing of the *Alicyclobacillus* sp. genomic clones were performed with an Applied Biosystems Model 3700 Automated DNA Sequencer using version 3.1 BIG-DYE™ terminator chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA). The sequences obtained were identical to the sequence from the genome sequencing (see example 1).

The nucleotide sequence and deduced amino acid sequence of the *Alicyclobacillus* sp. D1426D gene are shown in SEQ ID NO: 1 and SEQ ID NO: 2, respectively. The coding sequence is 1535 bp including the stop codon. The encoded predicted protein is 511 amino acids. Using the SignalP program (Nielsen et al., 1997, *Protein Engineering* 10: 1-6), a signal peptide of 25 residues was predicted.

Example 4. Construction of *Bacillus* Expression Vector Containing *Alicyclobacillus* sp. Genomic Sequence Encoding the M4 Metalloprotease Polypeptide of SEQ ID NO: 4

Two PCR primers were designed to amplify the genomic DNA sequence encoding the M4 metalloprotease of SEQ ID NO: 4:

```
D726XU.f:
                                          (SEQ ID NO. 7)
TTTTCTGTATTGACGTACTATTCTGAGATG

D726XU.r:
                                          (SEQ ID NO: 8)
ACTGTTTAAATACTACGATAATTTCGCAG
```

A first PCR amplification was performed in order to amplify the genomic sequence of SEQ ID NO: 3.
1 µl Genomic *Alicyclobacillus* sp. O2525 DNA (10.4 ng/µl)
0.5 µl Primer D726XU.f (100 pmol/µl)
0.5 µl Primer D726XU.r (100 pmol/µl)
2 µl dNTP (10 mM)
10 µl Buffer HF (5×)
0.5 µl Phusion polymerase
34.5 µl water.

The Phusion polymerase and the Buffer HF was provided from Finnzymes and used according to the manufacturers instructions.

The PCR reaction mixture was subjected to a programme of
1. 98° C. for 30 min
2. 98° C. for 10 s
3. 52° C. for 20 s
4. 72° C. for 90 s
5. Steps 2 to 4 was repeated 35 times
6. 72° C. for 10 min
7. Soak at 4° C.

5 µl of the reaction mixture was run on a agarose gel and a band in the expected size was observed. This first PCR reaction mixture was used as template DNA for a second PCR using the same primers and conditions described in example 2.

The resulting PCR reaction mixture from the second PCR was used as template for a SOE PCR fusion resulting in the fusion with control elements and resulting in an expression cassette, performed as described in example 2 and WO 99/43835, and transformants comprising the *Alicyclobacillus* sp. O2525 D726XU gene having SEQ ID NO: 3 were isolated.

Transformants were plated on LB+ 6 µg/ml Chloramplenicom+skimmed milk at 37° C. over night. Clearing halos were observed around the colonies indicating that the colonies produced active protease, whereas controls without the *Alicyclobacillus* sp. Metalloprotease gene did not give any halos.

Example 5. Characterization of the *Alicyclobacillus* sp. O2525 Genomic Sequence Having SEQ ID NO: 3 and Encoding a Polypeptide Having Protease Activity DNA sequencing of the *Alicyclobacillus* sp. O2525 genomic clones were performed with an Applied Biosystems Model 3700 Automated DNA Sequencer using version 3.1 BIG-DYE™ terminator chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA). The sequences obtained were identical to the sequence from the genome sequencing (see example 1).

The nucleotide sequence and deduced amino acid sequence of the *Alicyclobacillus* sp. D726XU gene are shown in SEQ ID NO: 3 and SEQ ID NO: 4, respectively. The coding sequence is 1554 bp including the stop codon. The encoded predicted protein is 517 amino acids. Using the SignalP program (Nielsen et al., 1997, *Protein Engineering* 10: 1-6), a signal peptide of 25 residues was predicted.

Example 6. Purification of the M4 Metalloprotease Having SEQ ID NO: 2

One expression clone obtained in example 2 was selected and was cultivated in rich medium on a rotary shaking table in 500 mL baffled Erlenmeyer flasks each containing 100 ml casein based media supplemented with 34 mg/l chloramphenicol. The clone was cultivated for 120 hours at 26° C. whereafter the flasks were harvested and the broth was pooled.

The culture broth was centrifuged (20000×g, 20 min) and the supernatant was carefully decanted from the precipitate. The supernatant was filtered through a Nalgene 0.2 µm filtration unit in order to remove the rest of the *Bacillus* host cells. The 0.2 µm filtrate was applied to a Bacitracin agarose column (from Upfront chromatography) equilibrated in 100 mM $H_3BO_3$, 10 mM MES, 2 mM $CaCl_2$, pH 6. After washing the column extensively with the equilibration buffer, the M4 protease was eluted with 100 mM $H_3BO_3$, 10 mM MES, 2 mM $CaCl_2$, 1 M NaCl, pH 6 with 25% (v/v) 2-propanol. Fractions from the column were analysed for protease activity (Protazyme AK purification activity assay at pH 7) and active fractions were further analysed by SDS-PAGE. Fractions, where only one band was seen on the coomassie stained SDS-PAGE gel, were pooled and transferred to 100 mM $H_3BO_3$, 10 mM MES, 2 mM $CaCl_2$, pH 6 on a G25 sephadex column as the purified preparation.

Example 7. Purification of the M4 Metalloprotease Having SEQ ID NO: 4

One expression clone obtained in example 4 was selected. The clone was cultivated and the metalloprotease purified using same methods as described in example 6.

Example 8. Characterization of the M4 Metalloproteases

The M4 metalloprotease having SEQ ID NO: 2 purified in example 6 and the M4 metalloprotease having SEQ ID NO: 4 purified in example 7 were subjected to N-terminal sequencing by EDMAN degradation, using an Applied Biosystems Procise Amino acid Sequencer Model 494 according to the manufacturer's instructions.

For the M4 metalloprotease having SEQ ID NO: 2 the N-terminal was determined as VAGTGTG corresponding to amino acids 214 to 220 in SEQ ID NO: 2. Thus the mature protein corresponds to amino acids 214 to 511 of SEQ ID NO: 2 and consists of 298 amino acids. Amino acids 1 to 25 of SEQ ID NO: 2 is the predicted signal sequence and amino acids 26 to 213 of SEQ ID NO: 2 is a propeptide. Mass spectroscopy analysis of the intact mature protein showed that the mature protein had the expected mass (data not shown).

For the M4 metalloprotease having SEQ ID NO: 4 the N-terminal was determined as DNTATAT corresponding to amino acids 214 to 220 in SEQ ID NO: 4. Thus the mature protein corresponds to amino acids 214 to 517 of SEQ ID NO: 4 and consists of 304 amino acids. Amino acids 1 to 25 of SEQ ID NO: 4 is the predicted signal sequence and amino acids 26 to 213 of SEQ ID NO: 4 is a propeptide. Mass spectroscopy analysis of the intact mature protein showed that the mature protein had the expected mass (data not shown).

Example 9. AMSA Wash Performance

The purified metalloproteases from examples 6 and 7 were tested in AMSA test as described above using the commercial protease Neutrase® (SEQ ID NO 9) as reference.

The following intensity values were obtained:

| | 2 g/L detergent, 20° C. | | | |
|---|---|---|---|---|
| | PC-05 | PC-03 | CS-37 | C-10 |
| Blank (no enzyme) | 260 | 372 | 310 | 394 |
| Reference (Neutrase ®) | 293 | 382 | 321 | 404 |

| 2 g/L detergent, 20° C. | | | | |
| --- | --- | --- | --- | --- |
|  | PC-05 | PC-03 | CS-37 | C-10 |
| Metalloprotease SEQ ID NO: 2 | 298 | 380 | 362 | 404 |
| Metalloprotease SEQ ID NO: 4 | 297 | 378 | 371 | 400 |

| 8 g/L detergent, 20° C. | | | | |
| --- | --- | --- | --- | --- |
|  | PC-05 | PC-03 | CS-37 | C-10 |
| Blank (no enzyme) | 277 | 375 | 373 | 395 |
| Reference (Neutrase ®) | 315 | 412 | 380 | 415 |
| Metalloprotease SEQ ID NO. 2 | 336 | 397 | 400 | 412 |
| Metalloprotease SEQ ID NO. 4 | 338 | 396 | 409 | 410 |

| 2 g/L detergent, 40° C. | | | | |
| --- | --- | --- | --- | --- |
|  | PC-05 | PC-03 | CS-37 | C-10 |
| Blank (no enzyme) | 268 | 355 | 316 | 384 |
| Reference (Neutrase ®) | 303 | 365 | 328 | 401 |
| Metalloprotease SEQ ID NO: 2 | 327 | 363 | 378 | 400 |
| Metalloprotease SEQ ID NO: 4 | 315 | 360 | 377 | 397 |

| 8 g/L detergent, 40° C. | | | | |
| --- | --- | --- | --- | --- |
|  | PC-05 | PC-03 | CS-37 | C-10 |
| Blank (no enzyme) | 293 | 358 | 377 | 387 |
| Reference (Neutrase ®) | 377 | 414 | 382 | 418 |
| Metalloprotease SEQ ID NO: 2 | 381 | 402 | 409 | 413 |
| Metalloprotease SEQ ID NO: 4 | 378 | 399 | 413 | 411 |

These result shows that the metalloproteases of the invention have a good performance in laundry and are on level or better that the commercial protease Neutrase®. The metalloproteases of the invention are performing particularly well on egg stains (CS-37) where the performance is above the reference under all the tested conditions.

The invention claimed is:

1. A method of cleaning laundry, hard surface, or dish, comprising washing the laundry, hard surface, or dish with a detergent composition comprising a polypeptide having protease activity and which has at least 80% sequence identity to the sequence of amino acids 214-511 of SEQ ID NO: 2 or the sequence of amino acids 214-517 of SEQ ID NO: 4.

2. The method of claim 1, wherein the polypeptide has at least 85% sequence identity to the sequence of amino acids 214-511 of SEQ ID NO: 2 or the sequence of amino acids 214-517 of SEQ ID NO: 4.

3. The method of claim 1, wherein the polypeptide has at least 90% sequence identity to the sequence of amino acids 214-511 of SEQ ID NO: 2 or the sequence of amino acids 214-517 of SEQ ID NO: 4.

4. The method of claim 1, wherein the polypeptide has at least 95% sequence identity to the sequence of amino acids 214-511 of SEQ ID NO: 2 or the sequence of amino acids 214-517 of SEQ ID NO: 4.

5. The method of claim 1, wherein the polypeptide is encoded by a polynucleotide that hybridizes under high stringency conditions with (i) the mature polypeptide coding sequence of SEQ ID NO: 1 or SEQ ID NO: 3, (ii) the cDNA sequence comprising the mature polypeptide coding sequence of SEQ ID NO: 1 or SEQ ID NO: 3, or (iii) the full-length complementary strand of (i) or (ii).

6. The method of claim 1, wherein the polypeptide is a variant comprising a substitution, deletion, and/or insertion of one or more amino acids of the sequence of amino acids 214-511 of SEQ ID NO: 2 or the sequence of amino acids 214-517 of SEQ ID NO: 4, wherein the variant has at least 85% sequence identity to the sequence of amino acids 214-511 of SEQ ID NO: 2 or the sequence of amino acids 214-517 of SEQ ID NO: 4.

7. The method of claim 1, wherein the polypeptide comprises the sequence of amino acids 214-511 of SEQ ID NO: 2.

8. The method of claim 1, wherein the polypeptide comprises the sequence of amino acids 214-517 of SEQ ID NO: 4.

9. The method of claim 1, wherein the polypeptide is a fragment of a polypeptide of the mature polypeptide of SEQ ID NO: 2 or SEQ ID NO: 4 that has protease activity, wherein the fragment has at least 85% sequence identity to the sequence of amino acids 214-511 of SEQ ID NO: 2 or the sequence of amino acids 214-517 of SEQ ID NO: 4.

10. The method of claim 1, wherein the detergent composition further comprises one or more additional enzymes selected from the group consisting of amylase, arabinase, carbohydrase, cellulase, cutinase, galactanase, lipase, mannanase, oxidase, pectinase, and xylanase.

11. The method of claim 1, wherein the detergent composition is in form of a bar, a homogenous tablet, a tablet having two or more layers, a pouch having one or more compartments, a regular or compact powder, a granule, a paste, a gel, or a regular, compact or concentrated liquid.

* * * * *

SEQUENCE LISTING

<160> NUMBER OF SEQ ID NOS: 9

<210> SEQ ID NO 1
<211> LENGTH: 1588
<212> TYPE: DNA
<213> ORGANISM: Alicyclobacillus species.
<220> FEATURE:
<221> NAME/KEY: CDS
<222> LOCATION: (53)..(1588)

<400> SEQUENCE: 1

```
cacagacgac agaatcgtct gaaaacaaag agaaacggga ggttacatca ga atg aac      58
                                                         Met Asn
                                                          1 aaa aag ctc atc acc acg ttg gtt atg tct tcc ctc gtt gca tcc gca     106
Lys Lys Leu Ile Thr Thr Leu Val Met Ser Ser Leu Val Ala Ser Ala
         5                  10                  15 ttc gca gtg aac gca ggc gct gct gtc acc gac aag caa gta ctg aaa     154
Phe Ala Val Asn Ala Gly Ala Ala Val Thr Asp Lys Gln Val Leu Lys
 20                  25                  30 gat gaa aac gcg aaa gtg cac acc gtt aac ggc cac ctc ggc aaa gta     202
Asp Glu Asn Ala Lys Val His Thr Val Asn Gly His Leu Gly Lys Val
 35                  40                  45                  50 tcc ggc gct acc agc gaa gct cgc gca atg gca gct ctc gac ctg gtt     250
Ser Gly Ala Thr Ser Glu Ala Arg Ala Met Ala Ala Leu Asp Leu Val
                 55                  60                  65 ggc aag gac ttc ggc ttt gca aaa gct gct ggc aac ttc gca gtc aaa     298
Gly Lys Asp Phe Gly Phe Ala Lys Ala Ala Gly Asn Phe Ala Val Lys
             70                  75                  80 gaa tcc cat gcc gat gag aat ggc gta gct cac acc aag ctc gac caa     346
Glu Ser His Ala Asp Glu Asn Gly Val Ala His Thr Lys Leu Asp Gln
         85                  90                  95
```

-continued

| | |
|---|---|
| acc atc aac ggc att aaa gtt ctt gac cat caa atg atc gtc cac gaa<br>Thr Ile Asn Gly Ile Lys Val Leu Asp His Gln Met Ile Val His Glu<br>100                     105                   110 | 394 |
| gca aac ggc gac gtt caa ggc gta acc ggc gac ttc gct caa gta acc<br>Ala Asn Gly Asp Val Gln Gly Val Thr Gly Asp Phe Ala Gln Val Thr<br>115                     120                   125                130 | 442 |
| ccg aac gct tcc aaa gcg gtt ctg tcc tcc gtt caa gcg gtt gac aaa<br>Pro Asn Ala Ser Lys Ala Val Leu Ser Ser Val Gln Ala Val Asp Lys<br>                 135                   140                  145 | 490 |
| gcg atc gca gcg acc ggc gta acc ggc caa ctg acc cac ccg gct acc<br>Ala Ile Ala Ala Thr Gly Val Thr Gly Gln Leu Thr His Pro Ala Thr<br>         150                   155                   160 | 538 |
| ggc gaa ctg acc tat gtt gtc gac ggc aac aag gca acc ctc gcg tac<br>Gly Glu Leu Thr Tyr Val Val Asp Gly Asn Lys Ala Thr Leu Ala Tyr<br>             165                   170                 175 | 586 |
| aaa gtc aac gtg gtc aac atc aac gca act caa ccg gtt cat tac gaa<br>Lys Val Asn Val Val Asn Ile Asn Ala Thr Gln Pro Val His Tyr Glu<br>180                     185                   190 | 634 |
| gtt ctg gtt gac gct gta aac ggc aac gtc ctc tcc tcc gtc aac ctg<br>Val Leu Val Asp Ala Val Asn Gly Asn Val Leu Ser Ser Val Asn Leu<br>195                     200                   205                210 | 682 |
| ctg gct gac gta gca ggt acc ggt acc ggc gtt ctg ggc gac aac aaa<br>Leu Ala Asp Val Ala Gly Thr Gly Thr Gly Val Leu Gly Asp Asn Lys<br>                 215                   220                  225 | 730 |
| acg atc caa acc acc tac aaa aac agc acc tac tac ctg gag gac cac<br>Thr Ile Gln Thr Thr Tyr Lys Asn Ser Thr Tyr Tyr Leu Glu Asp His<br>                 230                   235                  240 | 778 |
| tcc aag gcg atg acc ggc gac atc gaa acc tac gac ctg aaa aac ggt<br>Ser Lys Ala Met Thr Gly Asp Ile Glu Thr Tyr Asp Leu Lys Asn Gly<br>         245                   250                   255 | 826 |
| acg tcg acc ggt tac tac atc acc tcc acc aac aaa ttc acg acg<br>Thr Ser Thr Gly Tyr Tyr Ile Thr Ser Thr Thr Asn Lys Phe Thr Thr<br>260                     265                   270 | 874 |
| acc gca cag cgc gcg ggc gtt gac gct cac tac tac gct ggc gtc gtg<br>Thr Ala Gln Arg Ala Gly Val Asp Ala His Tyr Tyr Ala Gly Val Val<br>275                     280                   285                290 | 922 |
| ttc gac tac tac aaa ggc ctc ggc cgc aac tct tgg gat aac gct ggt<br>Phe Asp Tyr Tyr Lys Gly Leu Gly Arg Asn Ser Trp Asp Asn Ala Gly<br>                   295                   300                  305 | 970 |
| tct tcg atc tac tcc tac gtc cac tac tcc acc aac tac aac aac gca<br>Ser Ser Ile Tyr Ser Tyr Val His Tyr Ser Thr Asn Tyr Asn Asn Ala<br>                 310                   315                  320 | 1018 |
| ttc tgg gac ggc tac gaa atg atc tac ggc gac ggc gac ggc acc acg<br>Phe Trp Asp Gly Tyr Glu Met Ile Tyr Gly Asp Gly Asp Gly Thr Thr<br>         325                   330                   335 | 1066 |
| ttc cgc aac ttc gcg gct ggt aaa gac gta atc gcg cac gaa ttg acc<br>Phe Arg Asn Phe Ala Ala Gly Lys Asp Val Ile Ala His Glu Leu Thr<br>340                     345                   350 | 1114 |
| cac gcc gtt acc caa acc acc tcg aac ctg acc tac agc aac caa tcc<br>His Ala Val Thr Gln Thr Thr Ser Asn Leu Thr Tyr Ser Asn Gln Ser<br>355                     360                   365                370 | 1162 |
| ggt gcg ctc aac gag tcc tgg tcc gac gca caa gca acc gtt gtg gac<br>Gly Ala Leu Asn Glu Ser Trp Ser Asp Ala Gln Ala Thr Val Val Asp<br>                 375                   380                  385 | 1210 |
| ggc gac gac tgg atg atc ggc gaa gac atc tac acc ccg aac act tcc<br>Gly Asp Asp Trp Met Ile Gly Glu Asp Ile Tyr Thr Pro Asn Thr Ser<br>                 390                   395                  400 | 1258 |
| ggc gac gct ctg cgc tac atg gac aac ccg gca aaa ggc ggc caa ccg<br>Gly Asp Ala Leu Arg Tyr Met Asp Asn Pro Ala Lys Gly Gly Gln Pro | 1306 |

```
                405                 410                 415
gcg aac atg tcc ggc tac gtg aac acc acc tcc gat aac ggc ggc gtt      1354
Ala Asn Met Ser Gly Tyr Val Asn Thr Thr Ser Asp Asn Gly Gly Val
Ala Asn Met Ser Gly Tyr Val Asn Thr Thr Ser Asp Asn Gly Gly Val
    420                 425                 430 cac acc aac tcc ggc atc ccg aac aaa gcg ttc tac aac ttc gca acc      1402
His Thr Asn Ser Gly Ile Pro Asn Lys Ala Phe Tyr Asn Phe Ala Thr
435                 440                 445                 450 gcg att ggc tcc cgc acc atc gct ggt aaa gtc tgg tac acg gct tcc      1450
Ala Ile Gly Ser Arg Thr Ile Ala Gly Lys Val Trp Tyr Thr Ala Ser
                455                 460                 465 cgt gac tac atg acc tct tcc acc aac ttc tcc ggt gca cgc gct gcg      1498
Arg Asp Tyr Met Thr Ser Ser Thr Asn Phe Ser Gly Ala Arg Ala Ala
        470                 475                 480 acc ctg tcc gct gta gcg gct ctg tac ggc tcc ggt tcc tcc tac tac      1546
Thr Leu Ser Ala Val Ala Ala Leu Tyr Gly Ser Gly Ser Ser Tyr Tyr
            485                 490                 495 tcc gct ctg caa tcc gca tgg agc aac gta ggc gtc aac taa              1588
Ser Ala Leu Gln Ser Ala Trp Ser Asn Val Gly Val Asn
500                 505                 510
```

<210> SEQ ID NO 2
<211> LENGTH: 511
<212> TYPE: PRT
<213> ORGANISM: Alicyclobacillus species.

<400> SEQUENCE: 2

```
Met Asn Lys Lys Leu Ile Thr Thr Leu Val Met Ser Ser Leu Val Ala
1               5                   10                  15

Ser Ala Phe Ala Val Asn Ala Gly Ala Val Thr Asp Lys Gln Val
            20                  25                  30

Leu Lys Asp Glu Asn Ala Lys Val His Thr Val Asn Gly His Leu Gly
        35                  40                  45

Lys Val Ser Gly Ala Thr Ser Glu Ala Arg Ala Met Ala Ala Leu Asp
    50                  55                  60

Leu Val Gly Lys Asp Phe Gly Phe Ala Lys Ala Gly Asn Phe Ala
65                  70                  75                  80

Val Lys Glu Ser His Ala Asp Glu Asn Gly Val Ala His Thr Lys Leu
                85                  90                  95

Asp Gln Thr Ile Asn Gly Ile Lys Val Leu Asp His Gln Met Ile Val
            100                 105                 110

His Glu Ala Asn Gly Asp Val Gln Gly Val Thr Gly Asp Phe Ala Gln
        115                 120                 125

Val Thr Pro Asn Ala Ser Lys Ala Val Leu Ser Ser Val Gln Ala Val
    130                 135                 140

Asp Lys Ala Ile Ala Ala Thr Gly Val Thr Gly Gln Leu Thr His Pro
145                 150                 155                 160

Ala Thr Gly Glu Leu Thr Tyr Val Val Asp Gly Asn Lys Ala Thr Leu
                165                 170                 175

Ala Tyr Lys Val Asn Val Val Asn Ile Asn Ala Thr Gln Pro Val His
            180                 185                 190

Tyr Glu Val Leu Val Asp Ala Val Asn Gly Asn Val Leu Ser Ser Val
        195                 200                 205

Asn Leu Leu Ala Asp Val Ala Gly Thr Gly Thr Gly Val Leu Gly Asp
    210                 215                 220

Asn Lys Thr Ile Gln Thr Thr Tyr Lys Asn Ser Thr Tyr Tyr Leu Glu
225                 230                 235                 240
```

```
Asp His Ser Lys Ala Met Thr Gly Asp Ile Glu Thr Tyr Asp Leu Lys
                245                 250                 255

Asn Gly Thr Ser Thr Gly Tyr Tyr Ile Thr Ser Thr Asn Lys Phe
        260                 265                 270

Thr Thr Thr Ala Gln Arg Ala Gly Val Asp Ala His Tyr Tyr Ala Gly
            275                 280                 285

Val Val Phe Asp Tyr Tyr Lys Gly Leu Gly Arg Asn Ser Trp Asp Asn
    290                 295                 300

Ala Gly Ser Ser Ile Tyr Ser Tyr Val His Tyr Ser Thr Asn Tyr Asn
305                 310                 315                 320

Asn Ala Phe Trp Asp Gly Tyr Glu Met Ile Tyr Gly Asp Gly Asp Gly
                325                 330                 335

Thr Thr Phe Arg Asn Phe Ala Ala Gly Lys Asp Val Ile Ala His Glu
            340                 345                 350

Leu Thr His Ala Val Thr Gln Thr Thr Ser Asn Leu Thr Tyr Ser Asn
        355                 360                 365

Gln Ser Gly Ala Leu Asn Glu Ser Trp Ser Asp Ala Gln Ala Thr Val
    370                 375                 380

Val Asp Gly Asp Asp Trp Met Ile Gly Glu Asp Ile Tyr Thr Pro Asn
385                 390                 395                 400

Thr Ser Gly Asp Ala Leu Arg Tyr Met Asp Asn Pro Ala Lys Gly Gly
                405                 410                 415

Gln Pro Ala Asn Met Ser Gly Tyr Val Asn Thr Thr Ser Asp Asn Gly
            420                 425                 430

Gly Val His Thr Asn Ser Gly Ile Pro Asn Lys Ala Phe Tyr Asn Phe
        435                 440                 445

Ala Thr Ala Ile Gly Ser Arg Thr Ile Ala Gly Lys Val Trp Tyr Thr
    450                 455                 460

Ala Ser Arg Asp Tyr Met Thr Ser Ser Thr Asn Phe Ser Gly Ala Arg
465                 470                 475                 480

Ala Ala Thr Leu Ser Ala Val Ala Ala Leu Tyr Gly Ser Gly Ser Ser
                485                 490                 495

Tyr Tyr Ser Ala Leu Gln Ser Ala Trp Ser Asn Val Gly Val Asn
            500                 505                 510

<210> SEQ ID NO 3
<211> LENGTH: 1751
<212> TYPE: DNA
<213> ORGANISM: Alicyclobacillus species.
<220> FEATURE:
<221> NAME/KEY: CDS
<222> LOCATION: (101)..(1654)

<400> SEQUENCE: 3 atatttttc tgtattgacg tactattctg agatgacgta gtattgtgcc aagggtcgca      60
cttaaaaaga cccagtataa aataaacgga ggtcatacga atg aac aaa aaa ctt     115
                                              Met Asn Lys Lys Leu
                                                1               5 atc acc acg ttg gtc atg tct tct ctc gtt gca tcc gct ttc gca atg     163
Ile Thr Thr Leu Val Met Ser Ser Leu Val Ala Ser Ala Phe Ala Met
            10                  15                  20 aac gca ggc gct gct gtc acc gac aag caa gtc atg aaa gac gaa aaa     211
Asn Ala Gly Ala Ala Val Thr Asp Lys Gln Val Met Lys Asp Glu Lys
                25                  30                  35 ggc aaa ctg cat aac gtt gcc ggc cac ctc ggc aaa gta tcc ggc gct     259
Gly Lys Leu His Asn Val Ala Gly His Leu Gly Lys Val Ser Gly Ala
        40                  45                  50
```

```
acc agc gaa gct cgc gca atg gca gct ctc gat ctg gtt ggc aag gac      307
Thr Ser Glu Ala Arg Ala Met Ala Ala Leu Asp Leu Val Gly Lys Asp
     55                  60                  65 ttc ggt ttc gca aaa gcg aac ggc aac ttc caa gtg aag agc tcc cac      355
Phe Gly Phe Ala Lys Ala Asn Gly Asn Phe Gln Val Lys Ser Ser His
 70                  75                  80                  85 aac gac gaa aac ggt ctg gct cac acc aag ctg gac caa gtg atc aac      403
Asn Asp Glu Asn Gly Leu Ala His Thr Lys Leu Asp Gln Val Ile Asn
                 90                  95                 100 ggc atc ccg gtc ttc gat cat caa atg atc gtt cac gaa gca aac ggt      451
Gly Ile Pro Val Phe Asp His Gln Met Ile Val His Glu Ala Asn Gly
                105                 110                 115 gac gta caa ggc gta acc ggc gac ttc gct caa gta acc ccg acc gca      499
Asp Val Gln Gly Val Thr Gly Asp Phe Ala Gln Val Thr Pro Thr Ala
        120                 125                 130 acc aaa gca gtt ctg tct tcg gtt gct gca tct gat aaa gca gtt gct      547
Thr Lys Ala Val Leu Ser Ser Val Ala Ala Ser Asp Lys Ala Val Ala
    135                 140                 145 tcc acc ggc ttc acc ggc aag ctg gac cgc ccg gcg acc gcg aac ctg      595
Ser Thr Gly Phe Thr Gly Lys Leu Asp Arg Pro Ala Thr Ala Asn Leu
150                 155                 160                 165 acc tac gtg gtt caa ggc gac aaa gca gtc ctc gcg tac caa gtc aac      643
Thr Tyr Val Val Gln Gly Asp Lys Ala Val Leu Ala Tyr Gln Val Asn
                170                 175                 180 gtt gcg tac aac gac tcc aaa gct ccg ggc aac tgg caa atc ttc gtc      691
Val Ala Tyr Asn Asp Ser Lys Ala Pro Gly Asn Trp Gln Ile Phe Val
                185                 190                 195 aac gcg gtt gat ggc tcg atc atc tcc tcg ttg aac acc gtc gac ttc      739
Asn Ala Val Asp Gly Ser Ile Ile Ser Ser Leu Asn Thr Val Asp Phe
            200                 205                 210 gac aac acc gca acc gct acg gcg acc ggc gtt ctc ggc gac tcc aaa      787
Asp Asn Thr Ala Thr Ala Thr Ala Thr Gly Val Leu Gly Asp Ser Lys
            215                 220                 225 acc atc aac acc tac tac tac acc tct tac aaa tcc tac tac ttg gaa      835
Thr Ile Asn Thr Tyr Tyr Tyr Thr Ser Tyr Lys Ser Tyr Tyr Leu Glu
230                 235                 240                 245 gac cac acc aag gct gga ctg acc tct gct ggt cat gac atc gag acc      883
Asp His Thr Lys Ala Gly Leu Thr Ser Ala Gly His Asp Ile Glu Thr
                250                 255                 260 tac acc tgg aaa aac ggt act tcc acg tac tac gac atc ccg tcc acc      931
Tyr Thr Trp Lys Asn Gly Thr Ser Thr Tyr Tyr Asp Ile Pro Ser Thr
                265                 270                 275 aac aac acc tgg acc gac aaa gca gca gta gac gct cac tac tac gct      979
Asn Asn Thr Trp Thr Asp Lys Ala Ala Val Asp Ala His Tyr Tyr Ala
            280                 285                 290 ggt aaa gtc tat gac tac tac ctc ggt ctc ggt cgt acc tct tgg gac     1027
Gly Lys Val Tyr Asp Tyr Tyr Leu Gly Leu Gly Arg Thr Ser Trp Asp
            295                 300                 305 ggc aaa ggc gcg tcg atc tac tcg acc gtc cac tac tcc acc aac tac     1075
Gly Lys Gly Ala Ser Ile Tyr Ser Thr Val His Tyr Ser Thr Asn Tyr
310                 315                 320                 325 aac aac gca tac tgg gat ggt tcc aaa atg gta tac ggc gac ggc gac     1123
Asn Asn Ala Tyr Trp Asp Gly Ser Lys Met Val Tyr Gly Asp Gly Asp
                330                 335                 340 ggt gta acc ttc cgt tcc ctg tcc ggc ggc ttt gac gta gac gcg cac     1171
Gly Val Thr Phe Arg Ser Leu Ser Gly Gly Phe Asp Val Asp Ala His
                345                 350                 355 gaa atg acc cac gct gtc acc caa act acg tcc aac ctg acc tac tcc     1219
Glu Met Thr His Ala Val Thr Gln Thr Thr Ser Asn Leu Thr Tyr Ser
```

```
aac caa tcc ggt gca ctc aac gag tct tgg tct gac gcg caa gca acc     1267
Asn Gln Ser Gly Ala Leu Asn Glu Ser Trp Ser Asp Ala Gln Ala Thr
375                 380                 385 gtc atg gat gga gac gac tgg atg atc ggc gaa gac gtc tac acc ccg     1315
Val Met Asp Gly Asp Asp Trp Met Ile Gly Glu Asp Val Tyr Thr Pro
390                 395                 400                 405 aac acc tcg ggc gac gct ctg cgc tac atg gac aac ccg gaa aaa ggc     1363
Asn Thr Ser Gly Asp Ala Leu Arg Tyr Met Asp Asn Pro Glu Lys Gly
            410                 415                 420 ggc caa ccg tcc acg atg tcc gca tat gtg aac acc acc tcc gat aac     1411
Gly Gln Pro Ser Thr Met Ser Ala Tyr Val Asn Thr Thr Ser Asp Asn
        425                 430                 435 ggc ggt gtt cac acc aac tcc ggc atc ccg aac aaa gcg ttc tac aac     1459
Gly Gly Val His Thr Asn Ser Gly Ile Pro Asn Lys Ala Phe Tyr Asn
    440                 445                 450 ttc gca acc gca atc ggt tcc cgc acc atc gct ggt aaa gtt tgg tat     1507
Phe Ala Thr Ala Ile Gly Ser Arg Thr Ile Ala Gly Lys Val Trp Tyr
455                 460                 465 gta gct tcc cgt gac tac atg acc tct tcc acc aac ttc tcc ggt gca     1555
Val Ala Ser Arg Asp Tyr Met Thr Ser Ser Thr Asn Phe Ser Gly Ala
470                 475                 480                 485 cgc gct gcg acc ctg tcc gct gta ggc gca ctg tac ggc acc acc tct     1603
Arg Ala Ala Thr Leu Ser Ala Val Gly Ala Leu Tyr Gly Thr Thr Ser
            490                 495                 500 tcc tac tac acc gcg ttg aaa acc gct tgg acc aac gta ggc gtc aac     1651
Ser Tyr Tyr Thr Ala Leu Lys Thr Ala Trp Thr Asn Val Gly Val Asn
        505                 510                 515 taa tcaacatctg caactgtgaa aaccccgtg ctgctggcc gcggggtttt            1704 tgcttcgttg acgatctctg cgaaattatc gtagtattta aacagtc                 1751

<210> SEQ ID NO 4
<211> LENGTH: 517
<212> TYPE: PRT
<213> ORGANISM: Alicyclobacillus species.

<400> SEQUENCE: 4

Met Asn Lys Lys Leu Ile Thr Thr Leu Val Met Ser Ser Leu Val Ala
1               5                   10                  15

Ser Ala Phe Ala Met Asn Ala Gly Ala Ala Val Thr Asp Lys Gln Val
            20                  25                  30

Met Lys Asp Glu Lys Gly Lys Leu His Asn Val Ala Gly His Leu Gly
        35                  40                  45

Lys Val Ser Gly Ala Thr Ser Glu Ala Arg Ala Met Ala Ala Leu Asp
    50                  55                  60

Leu Val Gly Lys Asp Phe Gly Phe Ala Lys Ala Asn Gly Asn Phe Gln
65                  70                  75                  80

Val Lys Ser Ser His Asn Asp Glu Asn Gly Leu Ala His Thr Lys Leu
                85                  90                  95

Asp Gln Val Ile Asn Gly Ile Pro Val Phe Asp His Gln Met Ile Val
            100                 105                 110

His Glu Ala Asn Gly Asp Val Gln Gly Val Thr Gly Asp Phe Ala Gln
        115                 120                 125

Val Thr Pro Thr Ala Thr Lys Ala Val Leu Ser Ser Val Ala Ala Ser
    130                 135                 140

Asp Lys Ala Val Ala Ser Thr Gly Phe Thr Gly Lys Leu Asp Arg Pro
145                 150                 155                 160
```

Ala Thr Ala Asn Leu Thr Tyr Val Val Gln Gly Asp Lys Ala Val Leu
            165                 170                 175

Ala Tyr Gln Val Asn Val Ala Tyr Asn Asp Ser Lys Ala Pro Gly Asn
        180                 185                 190

Trp Gln Ile Phe Val Asn Ala Val Asp Gly Ser Ile Ile Ser Ser Leu
            195                 200                 205

Asn Thr Val Asp Phe Asp Asn Thr Ala Thr Ala Thr Ala Thr Gly Val
    210                 215                 220

Leu Gly Asp Ser Lys Thr Ile Asn Thr Tyr Tyr Thr Ser Tyr Lys
225                 230                 235                 240

Ser Tyr Tyr Leu Glu Asp His Thr Lys Ala Gly Leu Thr Ser Ala Gly
            245                 250                 255

His Asp Ile Glu Thr Tyr Thr Trp Lys Asn Gly Thr Ser Thr Tyr Tyr
            260                 265                 270

Asp Ile Pro Ser Thr Asn Asn Thr Trp Thr Asp Lys Ala Ala Val Asp
            275                 280                 285

Ala His Tyr Tyr Ala Gly Lys Val Tyr Asp Tyr Tyr Leu Gly Leu Gly
        290                 295                 300

Arg Thr Ser Trp Asp Gly Lys Gly Ala Ser Ile Tyr Ser Thr Val His
305                 310                 315                 320

Tyr Ser Thr Asn Tyr Asn Asn Ala Tyr Trp Asp Gly Ser Lys Met Val
            325                 330                 335

Tyr Gly Asp Gly Asp Gly Val Thr Phe Arg Ser Leu Ser Gly Gly Phe
        340                 345                 350

Asp Val Asp Ala His Glu Met Thr His Ala Val Thr Gln Thr Thr Ser
        355                 360                 365

Asn Leu Thr Tyr Ser Asn Gln Ser Gly Ala Leu Asn Glu Ser Trp Ser
    370                 375                 380

Asp Ala Gln Ala Thr Val Met Asp Gly Asp Trp Met Ile Gly Glu
385                 390                 395                 400

Asp Val Tyr Thr Pro Asn Thr Ser Gly Asp Ala Leu Arg Tyr Met Asp
            405                 410                 415

Asn Pro Glu Lys Gly Gly Gln Pro Ser Thr Met Ser Ala Tyr Val Asn
        420                 425                 430

Thr Thr Ser Asp Asn Gly Gly Val His Thr Asn Ser Gly Ile Pro Asn
            435                 440                 445

Lys Ala Phe Tyr Asn Phe Ala Thr Ala Ile Gly Ser Arg Thr Ile Ala
    450                 455                 460

Gly Lys Val Trp Tyr Val Ala Ser Arg Asp Tyr Met Thr Ser Ser Thr
465                 470                 475                 480

Asn Phe Ser Gly Ala Arg Ala Ala Thr Leu Ser Ala Val Gly Ala Leu
            485                 490                 495

Tyr Gly Thr Thr Ser Ser Tyr Tyr Thr Ala Leu Lys Thr Ala Trp Thr
            500                 505                 510

Asn Val Gly Val Asn
        515

<210> SEQ ID NO 5
<211> LENGTH: 38
<212> TYPE: DNA
<213> ORGANISM: Artificial sequence
<220> FEATURE:
<223> OTHER INFORMATION: Synthetic construct

<400> SEQUENCE: 5
gttcatcgat cgcatcggct gctgtcaccg acaagcaa    38

<210> SEQ ID NO 6
<211> LENGTH: 39
<212> TYPE: DNA
<213> ORGANISM: Artificial sequence
<220> FEATURE:
<223> OTHER INFORMATION: Synthetic construct

<400> SEQUENCE: 6
ccaaggccgg tttttatgt tttagttgac gcctacgtt    39

<210> SEQ ID NO 7
<211> LENGTH: 30
<212> TYPE: DNA
<213> ORGANISM: Artificial sequence
<220> FEATURE:
<223> OTHER INFORMATION: Synthetic construct

<400> SEQUENCE: 7
ttttctgtat tgacgtacta ttctgagatg    30

<210> SEQ ID NO 8
<211> LENGTH: 29
<212> TYPE: DNA
<213> ORGANISM: Artificial sequence
<220> FEATURE:
<223> OTHER INFORMATION: Synthetic construct

<400> SEQUENCE: 8
actgtttaaa tactacgata atttcgcag    29

<210> SEQ ID NO 9
<211> LENGTH: 300
<212> TYPE: PRT
<213> ORGANISM: bacillus amyloliquefaciens

<400> SEQUENCE: 9

Ala Ala Thr Thr Gly Thr Gly Thr Thr Leu Lys Gly Lys Thr Val Ser
1               5                   10                  15

Leu Asn Ile Ser Ser Glu Ser Gly Lys Tyr Val Leu Arg Asp Leu Ser
                20                  25                  30

Lys Pro Thr Gly Thr Gln Ile Ile Thr Tyr Asp Leu Gln Asn Arg Glu
            35                  40                  45

Tyr Asn Leu Pro Gly Thr Leu Val Ser Thr Thr Asn Gln Phe Thr
        50                  55                  60

Thr Ser Ser Gln Arg Ala Ala Val Asp Ala His Tyr Asn Leu Gly Lys
65                  70                  75                  80

Val Tyr Asp Tyr Phe Tyr Gln Lys Phe Asn Arg Asn Ser Tyr Asp Asn
                85                  90                  95

Lys Gly Gly Lys Ile Val Ser Ser Val His Tyr Gly Ser Arg Tyr Asn
            100                 105                 110

Asn Ala Ala Trp Ile Gly Asp Gln Met Ile Tyr Gly Asp Gly Asp Gly
        115                 120                 125

Ser Phe Phe Ser Pro Leu Ser Gly Ser Met Asp Val Thr Ala His Glu
    130                 135                 140

Met Thr His Gly Val Thr Gln Glu Thr Ala Asn Leu Asn Tyr Glu Asn
145                 150                 155                 160

Gln Pro Gly Ala Leu Asn Glu Ser Phe Ser Asp Val Phe Gly Tyr Phe
                165                 170                 175

```
Asn Asp Thr Glu Asp Trp Asp Ile Gly Glu Asp Ile Thr Val Ser Gln
            180             185             190

Pro Ala Leu Arg Ser Leu Ser Asn Pro Thr Lys Tyr Gly Gln Pro Asp
            195             200             205

Asn Phe Lys Asn Tyr Lys Asn Leu Pro Asn Thr Asp Ala Gly Asp Tyr
        210             215             220

Gly Gly Val His Thr Asn Ser Gly Ile Pro Asn Lys Ala Ala Tyr Asn
225             230             235             240

Thr Ile Thr Lys Ile Gly Val Asn Lys Ala Glu Gln Ile Tyr Tyr Arg
                245             250             255

Ala Leu Thr Val Tyr Leu Thr Pro Ser Ser Thr Phe Lys Asp Ala Lys
            260             265             270

Ala Ala Leu Ile Gln Ser Ala Arg Asp Leu Tyr Gly Ser Gln Asp Ala
        275             280             285

Ala Ser Val Glu Ala Ala Trp Asn Ala Val Gly Leu
    290             295             300
```